(12) United States Patent
Dlugos

(10) Patent No.: US 8,066,629 B2
(45) Date of Patent: Nov. 29, 2011

(54) APPARATUS FOR ADJUSTMENT AND SENSING OF GASTRIC BAND PRESSURE

(75) Inventor: Daniel F. Dlugos, Middletown, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1311 days.

(21) Appl. No.: 11/673,642

(22) Filed: Feb. 12, 2007

(65) Prior Publication Data
US 2007/0235083 A1  Oct. 11, 2007

Related U.S. Application Data

(63) Continuation-in-part of application No. 11/369,389, filed on Mar. 7, 2006, now Pat. No. 8,016,744, which is a continuation-in-part of application No. 11/065,410, filed on Feb. 24, 2005, now Pat. No. 7,699,770.

(51) Int. Cl.
 *A61F 2/00* (2006.01)
(52) U.S. Cl. ....................... 600/37; 604/97.02
(58) Field of Classification Search ............. 600/29–32, 600/37, 593; 128/897–899; 604/27–28, 604/909, 97.02; 607/41; 606/139–141, 157, 606/201–203, 213, 228, 151
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |

(Continued)

FOREIGN PATENT DOCUMENTS
AU  729 467  2/2001
(Continued)

OTHER PUBLICATIONS

U.S. Appl. No. 12/039,014, filed Feb. 28, 2008, Dlugos, Jr. et al.
(Continued)

*Primary Examiner* — John Lacyk
(74) *Attorney, Agent, or Firm* — Frost Brown Todd LLC

(57) ABSTRACT

An apparatus is operable to communicate fluid. An exemplary apparatus comprises a housing and a fluid reservoir within the housing. An actuator is operationally engaged with the fluid reservoir. The actuator is operable to effect communication of fluid from or into the fluid reservoir. A sensor is in fluid communication with the fluid reservoir. The sensor is operable to sense a physical parameter of fluid that is in communication with the fluid reservoir as the fluid is communicated from or into the fluid reservoir. An indicator is in communication with the sensor. The indicator is operable to display the physical parameter sensed by the sensor. The apparatus may be used to inject fluid into or withdraw fluid from an implanted gastric band system or for a variety of other uses. Fluid pressure may be adjusted and sensed, and resulting data may be displayed, by a single, integrated instrument.

20 Claims, 12 Drawing Sheets

U.S. PATENT DOCUMENTS

| | | | |
|---|---|---|---|
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Battenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,780,704 A | 11/1930 | Woodruff et al. |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Oden'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,178,463 A | 10/1939 | Bahnson |
| 2,180,599 A | 11/1939 | Menasco |
| 2,177,564 A | 12/1939 | Havill |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,396,351 A | 3/1946 | Thompson |
| 2,426,392 A | 8/1947 | Fennema |
| 2,426,817 A | 9/1947 | Carlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,581,479 A | 1/1950 | Grashman |
| 2,509,210 A | 5/1950 | Clark |
| 2,509,673 A | 5/1950 | Church |
| 2,511,765 A | 6/1950 | Bradbury |
| 2,520,056 A | 8/1950 | Posun |
| 2,521,976 A | 9/1950 | Hays |
| 2,533,924 A | 12/1950 | Foley |
| 2,538,259 A | 1/1951 | Merriman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |

| | | | | | |
|---|---|---|---|---|---|
| 3,187,181 A | 6/1965 | Keller | 3,482,449 A | 12/1969 | Werner |
| 3,187,745 A | 6/1965 | Baum et al. | 3,482,816 A | 12/1969 | Arnold |
| 3,190,388 A | 6/1965 | Moser et al. | 3,487,959 A | 1/1970 | Pearne et al. |
| 3,205,547 A | 9/1965 | Riekse | 3,491,842 A | 1/1970 | Delacour et al. |
| 3,208,255 A | 9/1965 | Burk | 3,492,638 A | 1/1970 | Lane |
| 3,209,570 A | 10/1965 | Hills | 3,502,829 A | 3/1970 | Reynolds |
| 3,221,468 A | 12/1965 | Casey | 3,503,116 A | 3/1970 | Strack |
| 3,228,703 A | 1/1966 | Wilson | 3,504,664 A | 4/1970 | Haddad |
| 3,229,684 A | 1/1966 | Nagumo et al. | 3,505,808 A | 4/1970 | Eschle |
| 3,236,088 A | 2/1966 | Moller | 3,509,754 A | 5/1970 | Massingill et al. |
| 3,238,624 A | 3/1966 | McCabe | 3,512,351 A | 5/1970 | Kadish et al. |
| 3,240,510 A | 3/1966 | Spouge | 3,514,919 A | 6/1970 | Ashton et al. |
| 3,245,642 A | 4/1966 | Dicke | 3,516,220 A | 6/1970 | Buford et al. |
| 3,255,568 A | 6/1966 | Martin et al. | 3,517,553 A | 6/1970 | Williams et al. |
| 3,260,091 A | 7/1966 | Shaw, Jr. | 3,527,226 A | 9/1970 | Hakin et al. |
| 3,265,822 A | 8/1966 | Moulten | 3,529,908 A | 9/1970 | Smith |
| 3,266,489 A | 8/1966 | Watkins et al. | 3,530,449 A | 9/1970 | Anderson |
| 3,273,447 A | 9/1966 | Frank | 3,533,403 A | 10/1970 | Woodson |
| 3,283,352 A | 11/1966 | Hu | 3,534,728 A | 10/1970 | Barrows |
| 3,290,919 A | 12/1966 | Malinak et al. | 3,534,872 A | 10/1970 | Roth et al. |
| 3,292,493 A | 12/1966 | Franklin | 3,535,914 A | 10/1970 | Veith et al. |
| 3,292,888 A | 12/1966 | Fischer | 3,539,009 A | 11/1970 | Kudlaty |
| 3,294,988 A | 12/1966 | Packard | 3,543,744 A | 12/1970 | LePar |
| 3,299,603 A | 1/1967 | Shaw | 3,545,275 A | 12/1970 | Harrison et al. |
| 3,299,882 A | 1/1967 | Masino | 3,550,583 A | 12/1970 | Chiku |
| 3,301,514 A | 1/1967 | Sugaya | 3,550,847 A | 12/1970 | Scott |
| 3,302,457 A | 2/1967 | Mayes | 3,563,094 A | 2/1971 | Rieschel |
| 3,306,384 A | 2/1967 | Ross | 3,563,245 A | 2/1971 | McLean et al. |
| 3,313,314 A | 4/1967 | Burke et al. | 3,566,083 A | 2/1971 | McMillin |
| 3,316,935 A | 5/1967 | Kaiser et al. | 3,566,875 A | 3/1971 | Stoehr |
| 3,320,750 A | 5/1967 | Haise et al. | 3,568,367 A | 3/1971 | Myers |
| 3,321,035 A | 5/1967 | Tarpley | 3,568,636 A | 3/1971 | Lockwood |
| 3,332,788 A | 7/1967 | Barnby | 3,576,554 A | 4/1971 | Temps, Jr. et al. |
| 3,334,510 A | 8/1967 | Hallesy | 3,580,082 A | 5/1971 | Strack |
| 3,339,401 A | 9/1967 | Peters | 3,581,402 A | 6/1971 | London et al. |
| 3,340,868 A | 9/1967 | Darling | 3,583,387 A | 6/1971 | Garner et al. |
| 3,347,162 A | 10/1967 | Braznell | 3,587,204 A | 6/1971 | George |
| 3,350,944 A | 11/1967 | De Michele | 3,590,809 A | 7/1971 | London |
| 3,353,364 A | 11/1967 | Blanding et al. | 3,590,818 A | 7/1971 | Lemole |
| 3,353,481 A | 11/1967 | Antonucci | 3,590,992 A | 7/1971 | Soderstrom et al. |
| 3,356,334 A | 12/1967 | Scaramucci | 3,592,183 A | 7/1971 | Watkins et al. |
| 3,356,510 A | 12/1967 | Barnby | 3,594,519 A | 7/1971 | Schmidlin |
| 3,357,218 A | 12/1967 | Mitchell | 3,602,885 A | 8/1971 | Grajeda |
| 3,357,461 A | 12/1967 | Friendship | 3,610,016 A | 10/1971 | Bultman |
| 3,359,741 A | 12/1967 | Nelson | 3,610,851 A | 10/1971 | Krupski |
| 3,361,300 A | 1/1968 | Kaplan | 3,611,811 A | 10/1971 | Lissau |
| 3,364,929 A | 1/1968 | Ide et al. | 3,614,926 A | 10/1971 | Brechtel |
| 3,365,684 A | 1/1968 | Stemke | 3,614,955 A | 10/1971 | Mirowski et al. |
| 3,378,456 A | 4/1968 | Roberts | 3,619,742 A | 11/1971 | Rud, Jr. |
| 3,380,445 A | 4/1968 | Frasier | 3,623,371 A | 11/1971 | Jullien-Davin |
| 3,380,649 A | 4/1968 | Roberts | 3,624,854 A | 12/1971 | Strong |
| 3,385,022 A | 5/1968 | Anderson | 3,630,242 A | 12/1971 | Schieser et al. |
| 3,389,355 A | 6/1968 | Schroeder, Jr. | 3,631,847 A | 1/1972 | Hobbs, II |
| 3,393,612 A | 7/1968 | Gorgens et al. | 3,633,881 A | 1/1972 | Yurdin |
| 3,396,561 A | 8/1968 | Day | 3,635,061 A | 1/1972 | Rydell et al. |
| 3,399,667 A | 9/1968 | Nishimoto et al. | 3,635,074 A | 1/1972 | Moos et al. |
| 3,400,734 A | 9/1968 | Rosenberg | 3,638,496 A | 2/1972 | King |
| 3,403,237 A | 9/1968 | Wysong | 3,644,883 A | 2/1972 | Borman et al. |
| 3,409,924 A | 11/1968 | Slama | 3,648,687 A | 3/1972 | Ramsey, III |
| 3,411,347 A | 11/1968 | Wirth et al. | 3,651,289 A | 3/1972 | Nagashima et al. |
| 3,417,476 A | 12/1968 | Martens | 3,651,405 A | 3/1972 | Whitney et al. |
| 3,420,325 A | 1/1969 | McAlister et al. | 3,653,671 A | 4/1972 | Shipes |
| 3,422,324 A | 1/1969 | Webb | 3,659,615 A | 5/1972 | Enger |
| 3,426,165 A | 2/1969 | Beaman | 3,677,685 A | 7/1972 | Aoki et al. |
| 3,438,391 A | 4/1969 | Yocum | 3,686,958 A | 8/1972 | Porter et al. |
| 3,443,608 A | 5/1969 | Copping et al. | 3,688,568 A | 9/1972 | Karper et al. |
| 3,445,335 A | 5/1969 | Gluntz | 3,701,392 A | 10/1972 | Wirth et al. |
| 3,447,281 A | 6/1969 | Bufford et al. | 3,702,677 A | 11/1972 | Heffington |
| 3,450,153 A | 6/1969 | Hildebrandt et al. | 3,703,099 A | 11/1972 | Rouse et al. |
| 3,453,546 A | 7/1969 | Fryer | 3,712,138 A | 1/1973 | Alinari et al. |
| 3,453,848 A | 7/1969 | Williamson | 3,713,124 A | 1/1973 | Durland et al. |
| 3,456,134 A | 7/1969 | Ko | 3,719,524 A | 3/1973 | Ripley et al. |
| 3,457,909 A | 7/1969 | Laird | 3,721,412 A | 3/1973 | Kindorf |
| 3,460,557 A | 8/1969 | Gallant | 3,723,247 A | 3/1973 | Leine et al. |
| 3,463,338 A | 8/1969 | Schneider | 3,724,000 A | 4/1973 | Eakman |
| 3,469,818 A | 9/1969 | Cowan | 3,727,463 A | 4/1973 | Intraub |
| 3,470,725 A | 10/1969 | Brown et al. | 3,727,615 A | 4/1973 | Lenzkes |
| 3,472,230 A | 10/1969 | Fogarty | 3,730,174 A | 5/1973 | Madison |
| 3,478,344 A | 11/1969 | Schwitzgebel et al. | 3,730,560 A | 5/1973 | Abildgaard et al. |

| | | | | | |
|---|---|---|---|---|---|
| 3,731,679 A | 5/1973 | Wilhelmson et al. | 3,908,334 A | 9/1975 | Rychiger et al. |
| 3,731,681 A | 5/1973 | Blackshear et al. | 3,908,461 A | 9/1975 | Turpen |
| 3,732,731 A | 5/1973 | Fussell, Jr. | 3,908,721 A | 9/1975 | McGahey et al. |
| 3,735,040 A | 5/1973 | Punt et al. | 3,910,087 A | 10/1975 | Jones |
| 3,736,930 A | 6/1973 | Georgi | 3,912,168 A | 10/1975 | Mullins et al. |
| 3,738,356 A | 6/1973 | Workman | 3,912,304 A | 10/1975 | Abildgaard et al. |
| 3,740,921 A | 6/1973 | Meyer et al. | 3,918,286 A | 11/1975 | Whitehead |
| 3,746,111 A | 7/1973 | Berthiaume et al. | 3,918,291 A | 11/1975 | Pauly et al. |
| 3,748,678 A | 7/1973 | Ballou | 3,920,965 A | 11/1975 | Sohrwardy et al. |
| 3,749,098 A | 7/1973 | De Bennetot et al. | 3,921,682 A | 11/1975 | McGahey et al. |
| 3,749,422 A | 7/1973 | Abildgaard et al. | 3,922,951 A | 12/1975 | Linsinger et al. |
| 3,749,423 A | 7/1973 | Abildgaard et al. | 3,923,060 A | 12/1975 | Ellinwood, Jr. |
| 3,750,194 A | 8/1973 | Summers | 3,924,635 A | 12/1975 | Hakim et al. |
| 3,757,770 A | 9/1973 | Brayshaw et al. | 3,928,980 A | 12/1975 | Ganzinotti et al. |
| 3,759,095 A | 9/1973 | Short, Jr. et al. | 3,929,175 A | 12/1975 | Coone |
| 3,760,638 A | 9/1973 | Lawson et al. | 3,930,682 A | 1/1976 | Booth |
| 3,763,960 A | 10/1973 | John et al. | 3,930,852 A | 1/1976 | Tanaka et al. |
| 3,765,142 A | 10/1973 | Lindquist et al. | 3,936,028 A | 2/1976 | Norton et al. |
| 3,765,494 A | 10/1973 | Kielman, Jr. | 3,939,823 A | 2/1976 | Kaye et al. |
| 3,769,156 A | 10/1973 | Brecy et al. | 3,940,122 A | 2/1976 | Janzen et al. |
| 3,769,830 A | 11/1973 | Porter et al. | 3,940,630 A | 2/1976 | Bergonz |
| 3,774,243 A | 11/1973 | Ny et al. | 3,942,299 A | 3/1976 | Bory et al. |
| 3,776,333 A | 12/1973 | Mathauser | 3,942,382 A | 3/1976 | Hok et al. |
| 3,778,051 A | 12/1973 | Allen et al. | 3,942,536 A | 3/1976 | Mirowski et al. |
| 3,780,578 A | 12/1973 | Sellman et al. | 3,943,915 A | 3/1976 | Severson |
| 3,781,902 A | 12/1973 | Shim et al. | 3,945,704 A | 3/1976 | Kraus et al. |
| 3,783,585 A | 1/1974 | Hoyland et al. | 3,946,613 A | 3/1976 | Silver |
| 3,789,667 A | 2/1974 | Porter et al. | 3,946,615 A | 3/1976 | Hluchan |
| 3,796,095 A | 3/1974 | Fussell, Jr. | 3,946,724 A | 3/1976 | La Balme et al. |
| 3,807,219 A | 4/1974 | Wallskog | 3,948,141 A | 4/1976 | Shinjo et al. |
| 3,811,429 A | 5/1974 | Fletcher et al. | 3,949,388 A | 4/1976 | Fuller |
| 3,815,722 A | 6/1974 | Sessoms | 3,953,289 A | 4/1976 | Costes et al. |
| 3,818,765 A | 6/1974 | Eriksen et al. | 3,954,271 A | 5/1976 | Tredway, Sr. |
| 3,820,400 A | 6/1974 | Russo | 3,958,558 A | 5/1976 | Dunphy et al. |
| 3,820,795 A | 6/1974 | Taylor | 3,960,142 A | 6/1976 | Elliott et al. |
| 3,823,610 A | 7/1974 | Fussell, Jr. | 3,961,425 A | 6/1976 | Swanson et al. |
| 3,825,065 A | 7/1974 | Lloyd et al. | 3,961,646 A | 6/1976 | Schon et al. |
| 3,825,963 A | 7/1974 | Abildgaard et al. | 3,962,895 A | 6/1976 | Rydell |
| 3,825,964 A | 7/1974 | Groswith, III et al. | 3,962,921 A | 6/1976 | Lips |
| 3,828,672 A | 8/1974 | Gazzola et al. | 3,963,019 A | 6/1976 | Quandt |
| 3,828,766 A | 8/1974 | Krasnow | 3,964,485 A | 6/1976 | Neumeier |
| 3,831,588 A | 8/1974 | Rindner | 3,964,770 A | 6/1976 | Abildgaard et al. |
| 3,831,942 A | 8/1974 | Del Mar | 3,967,737 A | 7/1976 | Peralta et al. |
| 3,833,238 A | 9/1974 | Liard et al. | 3,968,473 A | 7/1976 | Patton et al. |
| 3,834,167 A | 9/1974 | Tabor | 3,968,594 A | 7/1976 | Kawakami |
| 3,834,739 A | 9/1974 | Abildgaard et al. | 3,972,320 A | 8/1976 | Kalman |
| 3,835,523 A | 9/1974 | Stansfield et al. | 3,973,753 A | 8/1976 | Wheeler |
| 3,839,708 A | 10/1974 | Bredesen et al. | 3,973,858 A | 8/1976 | Poisson et al. |
| 3,842,483 A | 10/1974 | Cramer | 3,974,655 A | 8/1976 | Halpern et al. |
| 3,842,668 A | 10/1974 | Lippke et al. | 3,974,865 A | 8/1976 | Fenton et al. |
| 3,845,664 A | 11/1974 | Perry, Jr. | 3,976,278 A | 8/1976 | Dye et al. |
| 3,845,751 A | 11/1974 | Runstetler | 3,977,391 A | 8/1976 | Fleischmann |
| 3,845,757 A | 11/1974 | Weyer | 3,980,871 A | 9/1976 | Lindstrom et al. |
| 3,847,434 A | 11/1974 | Weman et al. | 3,982,571 A | 9/1976 | Fenton et al. |
| 3,850,208 A | 11/1974 | Hamilton | 3,983,948 A | 10/1976 | Jeter |
| 3,853,117 A | 12/1974 | Murr | 3,985,133 A | 10/1976 | Jenkins et al. |
| 3,854,469 A | 12/1974 | Giori et al. | 3,987,860 A | 10/1976 | Jabsen |
| 3,855,902 A | 12/1974 | Kirst et al. | 3,989,005 A | 11/1976 | Bowler, Jr. et al. |
| 3,857,399 A | 12/1974 | Zacouto et al. | 3,991,749 A | 11/1976 | Zent |
| 3,857,452 A | 12/1974 | Hartman | 3,992,948 A | 11/1976 | D'Antonio et al. |
| 3,857,745 A | 12/1974 | Grausch et al. | 3,993,149 A | 11/1976 | Harvey |
| 3,858,581 A | 1/1975 | Kamen | 3,996,927 A | 12/1976 | Frank |
| 3,863,622 A | 2/1975 | Buuck | 3,996,962 A | 12/1976 | Sutherland |
| 3,863,933 A | 2/1975 | Tredway | 4,003,141 A | 1/1977 | Le Roy |
| 3,867,950 A | 2/1975 | Fischell | 4,005,282 A | 1/1977 | Jennings |
| 3,868,008 A | 2/1975 | Brumbaugh | 4,005,593 A | 2/1977 | Goldberg |
| 3,868,679 A | 2/1975 | Arneson | 4,006,735 A | 2/1977 | Hittman et al. |
| 3,871,599 A | 3/1975 | Takada et al. | 4,009,375 A | 2/1977 | White et al. |
| 3,872,285 A | 3/1975 | Shum et al. | 4,009,591 A | 3/1977 | Hester |
| 3,874,388 A | 4/1975 | King et al. | 4,010,449 A | 3/1977 | Faggin et al. |
| 3,876,980 A | 4/1975 | Haemmig et al. | 4,014,319 A | 3/1977 | Favre et al. |
| 3,878,908 A | 4/1975 | Andersson et al. | 4,014,321 A | 3/1977 | March |
| 3,881,528 A | 5/1975 | Mackenzie | 4,016,764 A | 4/1977 | Rice |
| 3,886,948 A | 6/1975 | Hakim et al. | 4,017,329 A | 4/1977 | Larson |
| 3,893,111 A | 7/1975 | Cotter | 4,018,134 A | 4/1977 | Linsinger et al. |
| 3,893,451 A | 7/1975 | Durand et al. | 4,022,190 A | 5/1977 | Meyer |
| 3,895,681 A | 7/1975 | Griffin et al. | 4,024,864 A | 5/1977 | Davies et al. |
| 3,899,862 A | 8/1975 | Muys et al. | 4,025,912 A | 5/1977 | Rice |
| 3,904,234 A | 9/1975 | Hill et al. | 4,026,276 A | 5/1977 | Chubbuck |

| | | |
|---|---|---|
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |
| 4,045,345 A | 8/1977 | Drori et al. |
| 4,047,296 A | 9/1977 | Ishida et al. |
| 4,047,851 A | 9/1977 | Bender |
| 4,048,494 A | 9/1977 | Liesting et al. |
| 4,048,879 A | 9/1977 | Cox |
| 4,049,004 A | 9/1977 | Walters |
| 4,051,338 A | 9/1977 | Harris, III |
| 4,052,991 A | 10/1977 | Zacouto et al. |
| 4,055,074 A | 10/1977 | Thimons et al. |
| 4,055,175 A | 10/1977 | Clemens et al. |
| 4,056,854 A | 11/1977 | Boretos et al. |
| 4,058,007 A | 11/1977 | Exner et al. |
| 4,062,351 A | 12/1977 | Hastwell et al. |
| 4,062,354 A | 12/1977 | Taylor et al. |
| 4,062,360 A | 12/1977 | Bentley |
| 4,063,439 A | 12/1977 | Besson et al. |
| 4,064,882 A | 12/1977 | Johnson et al. |
| 4,070,239 A | 1/1978 | Bevilacqua |
| 4,072,047 A | 2/1978 | Reismuller et al. |
| 4,073,292 A | 2/1978 | Edelman |
| 4,075,099 A | 2/1978 | Pelton et al. |
| 4,075,602 A | 2/1978 | Clothier |
| 4,077,072 A | 3/1978 | Dezura et al. |
| 4,077,394 A | 3/1978 | McCurdy |
| 4,077,405 A | 3/1978 | Haerten et al. |
| 4,077,882 A | 3/1978 | Gangemi |
| 4,078,620 A | 3/1978 | Westlake et al. |
| 4,080,653 A | 3/1978 | Barnes, Jr. et al. |
| 4,084,752 A | 4/1978 | Hagiwara et al. |
| 4,086,488 A | 4/1978 | Hill |
| 4,087,568 A | 5/1978 | Fay et al. |
| 4,088,417 A | 5/1978 | Kosmowski |
| 4,089,329 A | 5/1978 | Couvillon, Jr. et al. |
| 4,090,802 A | 5/1978 | Bilz et al. |
| 4,092,719 A | 5/1978 | Salmon et al. |
| 4,092,925 A | 6/1978 | Fromson |
| 4,096,866 A | 6/1978 | Fischell |
| 4,098,293 A | 7/1978 | Kramer et al. |
| 4,103,496 A | 8/1978 | Colamussi et al. |
| 4,106,370 A | 8/1978 | Kraus et al. |
| 4,107,689 A | 8/1978 | Jellinek |
| 4,107,995 A | 8/1978 | Ligman et al. |
| 4,108,148 A | 8/1978 | Cannon, III |
| 4,108,575 A | 8/1978 | Schal et al. |
| 4,109,148 A | 8/1978 | Jaulmes et al. |
| 4,109,518 A | 8/1978 | Dooley et al. |
| 4,109,644 A | 8/1978 | Kojima |
| 4,111,056 A | 9/1978 | Mastromatteo |
| 4,111,629 A | 9/1978 | Nussbaumer et al. |
| 4,114,424 A | 9/1978 | Johnson |
| 4,114,603 A | 9/1978 | Wilkinson |
| 4,114,606 A | 9/1978 | Seylar |
| 4,120,097 A | 10/1978 | Jeter |
| 4,120,134 A | 10/1978 | Scholle |
| 4,121,635 A | 10/1978 | Hansel |
| 4,123,310 A | 10/1978 | Varon et al. |
| 4,124,023 A | 11/1978 | Fleischmann et al. |
| 4,127,110 A | 11/1978 | Bullara |
| 4,130,169 A | 12/1978 | Denison |
| 4,131,596 A | 12/1978 | Allen |
| 4,133,355 A | 1/1979 | Mayer |
| 4,133,367 A | 1/1979 | Abell |
| 4,135,509 A | 1/1979 | Shannon |
| 4,140,131 A | 2/1979 | Dutcher et al. |
| 4,141,348 A | 2/1979 | Hittman |
| 4,141,349 A | 2/1979 | Ory et al. |
| 4,143,661 A | 3/1979 | LaForge et al. |
| 4,146,029 A | 3/1979 | Ellinwood, Jr. |
| 4,147,161 A | 4/1979 | Ikebe et al. |
| 4,148,096 A | 4/1979 | Haas et al. |
| 4,149,423 A | 4/1979 | Frosch et al. |
| 4,151,823 A | 5/1979 | Grosse et al. |
| 4,153,085 A | 5/1979 | Adams |
| 4,156,422 A | 5/1979 | Hildebrandt et al. |
| 4,160,448 A | 7/1979 | Jackson |
| 4,160,971 A | 7/1979 | Jones et al. |
| 4,166,469 A | 9/1979 | Littleford |
| 4,167,304 A | 9/1979 | Gelbke |
| 4,167,952 A | 9/1979 | Reinicke |
| 4,168,567 A | 9/1979 | Leguy et al. |
| 4,170,280 A | 10/1979 | Schwarz |
| 4,171,218 A | 10/1979 | Hoshino et al. |
| 4,173,228 A | 11/1979 | Van Steenwyk et al. |
| 4,183,124 A | 1/1980 | Hoffman |
| 4,183,247 A | 1/1980 | Allen et al. |
| 4,185,641 A | 1/1980 | Minior et al. |
| 4,186,287 A | 1/1980 | Scott |
| 4,186,749 A | 2/1980 | Fryer |
| 4,186,751 A | 2/1980 | Fleischmann |
| 4,190,057 A | 2/1980 | Hill et al. |
| 4,191,004 A | 3/1980 | Gmuer et al. |
| 4,191,187 A | 3/1980 | Wright et al. |
| 4,192,192 A | 3/1980 | Schnell |
| 4,193,397 A | 3/1980 | Tucker et al. |
| 4,204,547 A | 5/1980 | Allocca |
| 4,206,755 A | 6/1980 | Klein et al. |
| 4,206,761 A | 6/1980 | Cosman |
| 4,206,762 A | 6/1980 | Cosman |
| 4,207,903 A | 6/1980 | O'Neill |
| 4,212,074 A | 7/1980 | Kuno et al. |
| 4,217,221 A | 8/1980 | Masso |
| 4,217,588 A | 8/1980 | Freeny, Jr. |
| 4,220,189 A | 9/1980 | Marquez |
| 4,221,219 A | 9/1980 | Tucker |
| 4,221,523 A | 9/1980 | Eberle |
| 4,223,837 A | 9/1980 | Gubbiotti et al. |
| 4,226,124 A | 10/1980 | Kersten et al. |
| 4,226,229 A | 10/1980 | Eckhart et al. |
| 4,227,533 A | 10/1980 | Godfrey |
| 4,231,376 A | 11/1980 | Lyon et al. |
| 4,232,682 A | 11/1980 | Veth |
| 4,237,900 A | 12/1980 | Schulman et al. |
| 4,241,247 A | 12/1980 | Byrne et al. |
| 4,241,870 A | 12/1980 | Marcus |
| 4,245,593 A | 1/1981 | Stein |
| 4,246,877 A | 1/1981 | Kennedy |
| 4,247,850 A | 1/1981 | Marcus |
| 4,248,238 A | 2/1981 | Joseph et al. |
| 4,248,241 A | 2/1981 | Tacchi |
| 4,256,094 A | 3/1981 | Kapp et al. |
| 4,256,118 A | 3/1981 | Nagel et al. |
| 4,262,343 A | 4/1981 | Claycomb |
| 4,262,632 A | 4/1981 | Hanton et al. |
| 4,265,241 A | 5/1981 | Portner et al. |
| 4,265,252 A | 5/1981 | Chubbuck et al. |
| 4,271,018 A | 6/1981 | Drori et al. |
| 4,273,070 A | 6/1981 | Hoefelmayr et al. |
| 4,274,444 A | 6/1981 | Ruyak |
| 4,275,600 A | 6/1981 | Turner et al. |
| 4,275,913 A | 6/1981 | Marcus |
| 4,278,540 A | 7/1981 | Drori et al. |
| 4,280,036 A | 7/1981 | Fukatsu et al. |
| 4,280,775 A | 7/1981 | Wood |
| 4,281,666 A | 8/1981 | Cosman |
| 4,281,667 A | 8/1981 | Cosman |
| 4,284,073 A | 8/1981 | Krause et al. |
| 4,285,770 A | 8/1981 | Chi et al. |
| 4,291,699 A | 9/1981 | Geddes et al. |
| 4,295,963 A | 10/1981 | Drori et al. |
| 4,297,927 A | 11/1981 | Kuroda et al. |
| 4,303,075 A | 12/1981 | Heilman et al. |
| 4,305,402 A | 12/1981 | Katims |
| 4,312,374 A | 1/1982 | Drori et al. |
| 4,314,480 A | 2/1982 | Becker |
| 4,316,693 A | 2/1982 | Baxter et al. |
| 4,325,387 A | 4/1982 | Helfer |
| 4,327,804 A | 5/1982 | Reed |
| 4,328,654 A | 5/1982 | Van Ginkel et al. |
| 4,332,254 A | 6/1982 | Lundquist |
| 4,332,255 A | 6/1982 | Hakim et al. |
| 4,339,831 A | 7/1982 | Johnson |
| 4,342,218 A | 8/1982 | Fox |

| | | |
|---|---|---|
| 4,342,308 A | 8/1982 | Trick |
| 4,346,604 A | 8/1982 | Snook et al. |
| 4,347,851 A | 9/1982 | Jundaniam |
| 4,350,647 A | 9/1982 | de la Cruz |
| 4,350,970 A | 9/1982 | von Tomkewitsch et al. |
| 4,351,037 A | 9/1982 | Scherbatskoy |
| 4,351,116 A | 9/1982 | Scott, Jr. |
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Schimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen |
| 4,378,809 A | 4/1983 | Cosman |
| 4,380,427 A | 4/1983 | Hehl et al. |
| 4,385,636 A | 5/1983 | Cosman |
| 4,386,422 A | 5/1983 | Mumby et al. |
| 4,387,715 A | 6/1983 | Hakim et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons et al. |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,124 A | 12/1983 | Marshall |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa et al. |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,450,946 A | 5/1984 | Olding et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm et al. |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,551,128 A | 11/1985 | Hakim et al. |
| 4,552,150 A | 11/1985 | Zacouto et al. |
| 4,553,226 A | 11/1985 | Scherbatskoy |
| 4,556,063 A | 12/1985 | Thompson et al. |
| 4,556,086 A | 12/1985 | Raines |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,749 A | 2/1986 | Fischell |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,595,390 A | 6/1986 | Hakim et al. |
| 4,596,563 A | 6/1986 | Pande |
| 4,599,943 A | 7/1986 | Kobler et al. |

| | | | | | | |
|---|---|---|---|---|---|---|
| 4,600,855 A | 7/1986 | Strachan et al. | | 4,757,463 A | 7/1988 | Ballou et al. |
| 4,602,541 A | 7/1986 | Benzinger et al. | | 4,759,386 A | 7/1988 | Grouw, III |
| 4,604,089 A | 8/1986 | Santangelo et al. | | 4,763,649 A | 8/1988 | Merrick |
| 4,605,354 A | 8/1986 | Daly | | 4,765,001 A | 8/1988 | Smith |
| 4,606,419 A | 8/1986 | Perini | | 4,767,406 A | 8/1988 | Wadham et al. |
| 4,606,478 A | 8/1986 | Hack et al. | | 4,769,001 A | 9/1988 | Prince |
| 4,610,256 A | 9/1986 | Wallace | | 4,772,257 A | 9/1988 | Hakim et al. |
| 4,614,137 A | 9/1986 | Jones | | 4,772,896 A | 9/1988 | Nakatsu et al. |
| 4,615,691 A | 10/1986 | Hakim et al. | | 4,773,401 A | 9/1988 | Citak et al. |
| 4,617,016 A | 10/1986 | Blomberg et al. | | 4,774,950 A | 10/1988 | Cohen |
| 4,618,861 A | 10/1986 | Gettens et al. | | 4,774,955 A | 10/1988 | Jones |
| 4,620,807 A | 11/1986 | Polit | | 4,777,953 A | 10/1988 | Ash et al. |
| 4,621,331 A | 11/1986 | Iwata et al. | | 4,779,626 A | 10/1988 | Peel et al. |
| 4,622,871 A | 11/1986 | Van Sickle et al. | | 4,781,192 A | 11/1988 | Demer |
| 4,626,462 A | 12/1986 | Kober et al. | | 4,782,826 A | 11/1988 | Fogarty |
| 4,633,304 A | 12/1986 | Nagasaki et al. | | 4,783,106 A | 11/1988 | Nutter |
| 4,633,878 A | 1/1987 | Bombardieri et al. | | 4,785,822 A | 11/1988 | Wallace |
| 4,635,182 A | 1/1987 | Hintz | | 4,788,847 A | 12/1988 | Sterghos |
| 4,637,736 A | 1/1987 | Andeen et al. | | 4,791,318 A | 12/1988 | Lewis et al. |
| 4,638,665 A | 1/1987 | Benson et al. | | 4,794,803 A | 1/1989 | Osterhout et al. |
| 4,644,246 A | 2/1987 | Knapen et al. | | 4,796,641 A | 1/1989 | Mills et al. |
| 4,646,553 A | 3/1987 | Tufte et al. | | 4,798,211 A | 1/1989 | Goor et al. |
| 4,648,363 A | 3/1987 | Kronich | | 4,798,227 A | 1/1989 | Goodwin |
| 4,648,406 A | 3/1987 | Miller | | 4,799,491 A | 1/1989 | Eckerle |
| 4,658,358 A | 4/1987 | Leach et al. | | 4,799,625 A | 1/1989 | Weaver, Jr. et al. |
| 4,658,760 A | 4/1987 | Zehuhr | | 4,802,488 A | 2/1989 | Eckerle |
| 4,660,568 A | 4/1987 | Cosman | | 4,803,987 A | 2/1989 | Calfee et al. |
| 4,665,511 A | 5/1987 | Rodney et al. | | 4,804,368 A | 2/1989 | Skakoon et al. |
| 4,665,896 A | 5/1987 | LaForge et al. | | 4,807,321 A | 2/1989 | Grasselli et al. |
| 4,669,484 A | 6/1987 | Masters | | 4,808,167 A | 2/1989 | Mann et al. |
| 4,672,974 A | 6/1987 | Lee | | 4,812,823 A | 3/1989 | Dickerson |
| 4,674,457 A | 6/1987 | Berger et al. | | 4,819,656 A | 4/1989 | Spector |
| 4,674,546 A | 6/1987 | Fournier et al. | | 4,820,265 A | 4/1989 | DeSatnick et al. |
| 4,678,408 A | 7/1987 | Nason et al. | | 4,820,953 A | 4/1989 | Saubolle et al. |
| 4,681,559 A | 7/1987 | Hooven | | 4,821,167 A | 4/1989 | Wiebe |
| 4,683,850 A | 8/1987 | Bauder et al. | | 4,821,723 A | 4/1989 | Baker, Jr. et al. |
| 4,685,463 A | 8/1987 | Williams | | 4,823,779 A | 4/1989 | Daly et al. |
| 4,685,469 A | 8/1987 | Keller et al. | | 4,830,006 A | 5/1989 | Haluska et al. |
| 4,685,903 A | 8/1987 | Cable et al. | | 4,832,034 A | 5/1989 | Pizziconi et al. |
| 4,686,987 A | 8/1987 | Salo et al. | | 4,833,384 A | 5/1989 | Munro et al. |
| 4,687,530 A | 8/1987 | Berscheid et al. | | 4,834,731 A | 5/1989 | Nowak et al. |
| 4,691,694 A | 9/1987 | Boyd et al. | | 4,838,857 A | 6/1989 | Strowe et al. |
| 4,691,710 A | 9/1987 | Dickens et al. | | 4,840,068 A | 6/1989 | Mayhew, Jr. |
| 4,693,253 A | 9/1987 | Adams | | 4,840,350 A | 6/1989 | Cook et al. |
| 4,695,237 A | 9/1987 | Inaba et al. | | 4,844,002 A | 7/1989 | Yasue et al. |
| 4,696,189 A | 9/1987 | Hochreuther et al. | | 4,846,153 A | 7/1989 | Berci |
| 4,697,574 A | 10/1987 | Karcher et al. | | 4,846,191 A | 7/1989 | Brockway et al. |
| 4,698,038 A | 10/1987 | Key et al. | | 4,846,664 A | 7/1989 | Hehl et al. |
| 4,700,497 A | 10/1987 | Sato et al. | | 4,854,328 A | 8/1989 | Pollack |
| 4,700,610 A | 10/1987 | Bauer et al. | | 4,863,470 A | 9/1989 | Carter |
| 4,701,143 A | 10/1987 | Key et al. | | 4,865,587 A | 9/1989 | Walling |
| 4,703,756 A | 11/1987 | Gough et al. | | 4,867,160 A | 9/1989 | Schaldach et al. |
| 4,705,507 A | 11/1987 | Boyles | | 4,867,498 A | 9/1989 | Delphia et al. |
| 4,706,948 A | 11/1987 | Kroecher et al. | | 4,867,618 A | 9/1989 | Brohammer |
| 4,711,249 A | 12/1987 | Brooks | | 4,869,252 A | 9/1989 | Gilli |
| 4,712,562 A | 12/1987 | Ohayon et al. | | 4,870,258 A | 9/1989 | Mochizuki et al. |
| 4,718,425 A | 1/1988 | Tanaka et al. | | 4,871,351 A | 10/1989 | Feingold et al. |
| 4,722,348 A | 2/1988 | Ligtenberg et al. | | 4,872,483 A | 10/1989 | Shah |
| 4,724,806 A | 2/1988 | Hartwig et al. | | 4,872,869 A | 10/1989 | Johns |
| 4,724,830 A | 2/1988 | Fischell | | 4,873,677 A | 10/1989 | Sakamoto et al. |
| 4,725,826 A | 2/1988 | Hunter | | 4,875,483 A | 10/1989 | Vollmann et al. |
| 4,727,887 A | 3/1988 | Haber | | 4,880,004 A | 11/1989 | Baker, Jr. et al. |
| 4,728,479 A | 3/1988 | Merkovsky | | 4,882,678 A | 11/1989 | Hollis et al. |
| 4,729,517 A | 3/1988 | Krokor et al. | | 4,886,392 A | 12/1989 | Iio et al. |
| 4,730,188 A | 3/1988 | Milheiser | | 4,893,630 A | 1/1990 | Bray, Jr. |
| 4,730,420 A | 3/1988 | Stratmann et al. | | 4,895,151 A | 1/1990 | Grevis et al. |
| 4,730,619 A | 3/1988 | Koning et al. | | 4,896,594 A | 1/1990 | Baur et al. |
| 4,731,058 A | 3/1988 | Doan | | 4,898,158 A | 2/1990 | Daly et al. |
| 4,735,205 A | 4/1988 | Chachques et al. | | 4,898,578 A | 2/1990 | Rubalcaba, Jr. |
| 4,738,267 A | 4/1988 | Lazorthes et al. | | 4,899,751 A | 2/1990 | Cohen |
| 4,738,268 A | 4/1988 | Kipnis | | 4,899,752 A | 2/1990 | Cohen |
| 4,741,345 A | 5/1988 | Matthews et al. | | 4,902,277 A | 2/1990 | Mathies et al. |
| 4,741,732 A | 5/1988 | Crankshaw et al. | | 4,903,701 A | 2/1990 | Moore et al. |
| 4,743,129 A | 5/1988 | Keryhuel et al. | | 4,905,698 A | 3/1990 | Strohl, Jr. et al. |
| 4,745,541 A | 5/1988 | Vaniglia et al. | | 4,909,678 A | 3/1990 | Kakimoto et al. |
| 4,746,830 A | 5/1988 | Holland | | 4,913,147 A | 4/1990 | Fahlstrom et al. |
| 4,750,495 A | 6/1988 | Moore et al. | | 4,919,143 A | 4/1990 | Ayers |
| 4,752,115 A | 6/1988 | Murray, Jr. et al. | | 4,924,872 A | 5/1990 | Frank |
| 4,752,658 A | 6/1988 | Mack | | 4,926,903 A | 5/1990 | Kawai et al. |

| | | | | | | |
|---|---|---|---|---|---|---|
| 4,932,406 A | 6/1990 | Berkovits | | 5,062,053 A | 10/1991 | Shirai et al. |
| 4,934,369 A | 6/1990 | Maxwell | | 5,064,974 A | 11/1991 | Vigneau et al. |
| 4,936,304 A | 6/1990 | Kresh et al. | | 5,067,960 A | 11/1991 | Grandjean et al. |
| 4,940,037 A | 7/1990 | Eckert et al. | | 5,068,779 A | 11/1991 | Sullivan et al. |
| 4,941,718 A | 7/1990 | Alexander, III et al. | | 5,069,680 A | 12/1991 | Grandjean et al. |
| 4,942,004 A | 7/1990 | Catanzaro | | 5,077,102 A | 12/1991 | Chong |
| 4,944,050 A | 7/1990 | Shames et al. | | 5,077,870 A | 1/1992 | Melbye et al. |
| 4,944,298 A | 7/1990 | Sholder | | 5,078,139 A | 1/1992 | Strand et al. |
| 4,944,307 A | 7/1990 | Hon et al. | | 5,082,006 A | 1/1992 | Jonasson et al. |
| 4,945,761 A | 8/1990 | Lessi et al. | | 5,083,563 A | 1/1992 | Collins et al. |
| 4,949,724 A | 8/1990 | Mahutte et al. | | 5,084,699 A | 1/1992 | DeMichele |
| 4,952,205 A | 8/1990 | Mauerer et al. | | 5,085,224 A | 2/1992 | Galen et al. |
| 4,952,928 A | 8/1990 | Carroll et al. | | 5,085,258 A | 2/1992 | Fink, Jr. et al. |
| 4,953,563 A | 9/1990 | Kaiser et al. | | 5,089,673 A | 2/1992 | Strzodka et al. |
| 4,954,677 A | 9/1990 | Alberter et al. | | 5,089,979 A | 2/1992 | McEachern et al. |
| 4,958,630 A | 9/1990 | Rosenbluth et al. | | 5,095,309 A | 3/1992 | Troyk et al. |
| 4,958,645 A | 9/1990 | Cadell et al. | | 5,096,271 A | 3/1992 | Portman |
| 4,960,424 A | 10/1990 | Grooters | | 5,097,831 A | 3/1992 | Lekholm |
| 4,960,966 A | 10/1990 | Evans et al. | | 5,098,384 A | 3/1992 | Abrams |
| 4,967,585 A | 11/1990 | Grimaldo | | 5,099,845 A | 3/1992 | Besz et al. |
| 4,967,761 A | 11/1990 | Nathanielsz | | 5,103,832 A | 4/1992 | Jackson |
| 4,970,823 A | 11/1990 | Chen et al. | | 5,105,810 A | 4/1992 | Collins et al. |
| 4,971,251 A | 11/1990 | Dobrick et al. | | 5,107,850 A | 4/1992 | Olive |
| 4,977,896 A | 12/1990 | Robinson et al. | | 5,112,344 A | 5/1992 | Petros et al. |
| 4,978,335 A | 12/1990 | Arthur, III | | 5,113,859 A | 5/1992 | Funke et al. |
| 4,978,338 A | 12/1990 | Melsky et al. | | 5,113,869 A | 5/1992 | Nappholz et al. |
| 4,979,730 A | 12/1990 | Holbrook et al. | | 5,115,676 A | 5/1992 | Lee |
| 4,980,671 A | 12/1990 | McCurdy | | 5,117,825 A | 6/1992 | Grevious |
| 4,981,141 A | 1/1991 | Segalowitz | | 5,120,313 A | 6/1992 | Elftman |
| 4,981,173 A | 1/1991 | Perkins et al. | | 5,121,777 A | 6/1992 | Leininger et al. |
| 4,981,426 A | 1/1991 | Aoki et al. | | 5,127,451 A | 7/1992 | Fink, Jr. et al. |
| 4,987,897 A | 1/1991 | Funke et al. | | 5,129,394 A | 7/1992 | Mehra |
| 4,988,337 A | 1/1991 | Ito et al. | | 5,129,806 A | 7/1992 | Hehl et al. |
| 4,992,794 A | 2/1991 | Brouwers et al. | | 5,131,145 A | 7/1992 | Badoureaux et al. |
| 4,997,556 A | 3/1991 | Yano et al. | | 5,131,388 A | 7/1992 | Pless et al. |
| 5,001,528 A | 3/1991 | Bahraman | | 5,133,358 A | 7/1992 | Gustafson et al. |
| 5,003,807 A | 4/1991 | Terrell et al. | | 5,135,488 A | 8/1992 | Foote et al. |
| 5,003,975 A | 4/1991 | Hafelfinger et al. | | 5,139,484 A | 8/1992 | Hazon et al. |
| 5,003,976 A | 4/1991 | Alt et al. | | 5,144,949 A | 9/1992 | Olson |
| 5,004,472 A | 4/1991 | Wallace | | 5,148,580 A | 9/1992 | Dyckow et al. |
| 5,004,873 A | 4/1991 | Schnut | | 5,148,695 A | 9/1992 | Ellis |
| 5,005,574 A | 4/1991 | Fearnot et al. | | 5,152,770 A | 10/1992 | Bangmark et al. |
| 5,005,586 A | 4/1991 | Lahr | | 5,152,776 A | 10/1992 | Pinchuk |
| 5,006,884 A | 4/1991 | Kazuhito et al. | | 5,154,170 A | 10/1992 | Bennett et al. |
| 5,006,997 A | 4/1991 | Reich | | 5,154,171 A | 10/1992 | Chirife et al. |
| 5,007,401 A | 4/1991 | Grohn et al. | | 5,154,693 A | 10/1992 | East et al. |
| 5,007,430 A | 4/1991 | Dardik | | 5,156,972 A | 10/1992 | Issachar et al. |
| 5,007,919 A | 4/1991 | Silva et al. | | 5,158,078 A | 10/1992 | Bennett et al. |
| 5,009,662 A | 4/1991 | Wallace et al. | | 5,163,429 A | 11/1992 | Cohen |
| 5,010,893 A | 4/1991 | Sholder | | 5,163,904 A | 11/1992 | Lampropoulos et al. |
| 5,012,286 A | 4/1991 | Kawano et al. | | 5,167,615 A | 12/1992 | East et al. |
| 5,012,810 A | 5/1991 | Strand et al. | | 5,168,757 A | 12/1992 | Rabenau et al. |
| 5,013,292 A | 5/1991 | Lemay et al. | | 5,168,982 A | 12/1992 | Hakanen et al. |
| 5,014,040 A | 5/1991 | Weaver et al. | | 5,171,299 A | 12/1992 | Heitzmann et al. |
| 5,019,032 A | 5/1991 | Robertson | | 5,173,873 A | 12/1992 | Wu et al. |
| 5,019,041 A | 5/1991 | Robinson et al. | | 5,174,286 A | 12/1992 | Chirige et al. |
| 5,020,845 A | 6/1991 | Falcoff et al. | | 5,174,291 A | 12/1992 | Schoonen et al. |
| 5,021,046 A | 6/1991 | Wallace | | 5,176,502 A | 1/1993 | Sanderson et al. |
| 5,022,395 A | 6/1991 | Russie | | 5,178,197 A | 1/1993 | Healy |
| 5,024,965 A | 6/1991 | Chang et al. | | 5,181,423 A | 1/1993 | Phillips et al. |
| 5,026,180 A | 6/1991 | Tajima et al. | | 5,181,517 A | 1/1993 | Hickey |
| 5,026,360 A | 6/1991 | Johnsen et al. | | 5,184,132 A | 2/1993 | Baird |
| 5,028,918 A | 7/1991 | Giles et al. | | 5,184,614 A | 2/1993 | Collins et al. |
| 5,032,822 A | 7/1991 | Sweet | | 5,184,619 A | 2/1993 | Austin |
| 5,036,869 A | 8/1991 | Inahara et al. | | 5,185,535 A | 2/1993 | Farb et al. |
| 5,038,800 A | 8/1991 | Oba et al. | | 5,186,224 A | 2/1993 | Schirmacher et al. |
| 5,041,086 A | 8/1991 | Koenig et al. | | 5,188,106 A | 2/1993 | Nappholz et al. |
| 5,041,826 A | 8/1991 | Milheiser | | 5,188,604 A | 2/1993 | Orth |
| 5,042,503 A | 8/1991 | Torok et al. | | 5,192,314 A | 3/1993 | Daskalakis |
| 5,044,770 A | 9/1991 | Haghkar | | 5,195,362 A | 3/1993 | Eason |
| 5,046,661 A | 9/1991 | Kimura et al. | | 5,197,322 A | 3/1993 | Indravudh |
| 5,048,060 A | 9/1991 | Arai et al. | | 5,199,427 A | 4/1993 | Strickland |
| 5,050,922 A | 9/1991 | Falcoff | | 5,199,428 A | 4/1993 | Obel et al. |
| 5,052,910 A | 10/1991 | Hehl et al. | | 5,201,753 A | 4/1993 | Lampropoulos et al. |
| 5,053,008 A | 10/1991 | Bajaj | | 5,204,670 A | 4/1993 | Stinton |
| 5,057,078 A | 10/1991 | Foote et al. | | 5,207,429 A | 5/1993 | Walmsley et al. |
| 5,058,583 A | 10/1991 | Geddes et al. | | 5,209,223 A | 5/1993 | McGorry et al. |
| 5,061,239 A | 10/1991 | Shiels | | 5,209,731 A * | 5/1993 | Sterman et al. ............ 604/97.02 |
| 5,062,052 A | 10/1991 | Sparer et al. | | 5,209,732 A | 5/1993 | Lampropoulos et al. |

| | | | | | |
|---|---|---|---|---|---|
| 5,211,129 A | 5/1993 | Taylor et al. | 5,394,909 A | 3/1995 | Mitchell et al. |
| 5,211,161 A | 5/1993 | Stef et al. | 5,396,899 A | 3/1995 | Strittmatter |
| 5,212,476 A | 5/1993 | Maloney | 5,402,944 A | 4/1995 | Pape et al. |
| 5,213,331 A | 5/1993 | Avanzini | 5,406,957 A | 4/1995 | Tansey |
| 5,215,523 A | 6/1993 | Williams et al. | 5,409,009 A | 4/1995 | Olson |
| 5,218,343 A | 6/1993 | Stobbe et al. | 5,411,031 A | 5/1995 | Yomtov |
| 5,218,957 A | 6/1993 | Strickland | 5,411,551 A | 5/1995 | Winston et al. |
| 5,226,429 A | 7/1993 | Kuzmak | 5,411,552 A | 5/1995 | Anderson et al. |
| 5,226,604 A | 7/1993 | Seiffert et al. | 5,416,372 A | 5/1995 | Ljungstroem et al. |
| 5,230,694 A | 7/1993 | Rosenblum | 5,417,226 A | 5/1995 | Juma |
| 5,233,985 A | 8/1993 | Hudrlik | 5,417,717 A | 5/1995 | Salo et al. |
| 5,235,326 A | 8/1993 | Beigel et al. | 5,425,362 A | 6/1995 | Siker et al. |
| 5,244,269 A | 9/1993 | Harriehausen et al. | 5,425,713 A | 6/1995 | Taylor et al. |
| 5,244,461 A | 9/1993 | Derlien et al. | 5,431,171 A | 7/1995 | Harrison et al. |
| 5,246,008 A | 9/1993 | Mueller et al. | 5,431,629 A | 7/1995 | Lampropoulos et al. |
| 5,249,858 A | 10/1993 | Nusser | 5,431,694 A | 7/1995 | Snaper et al. |
| 5,250,020 A | 10/1993 | Bley | 5,433,694 A | 7/1995 | Lim |
| 5,254,096 A | 10/1993 | Rondelet et al. | 5,437,605 A | 8/1995 | Helmy et al. |
| 5,256,157 A | 10/1993 | Samiotes et al. | 5,443,215 A | 8/1995 | Fackler |
| 5,263,244 A | 11/1993 | Centa et al. | 5,447,519 A | 9/1995 | Peterson |
| 5,263,981 A | 11/1993 | Polyak et al. | 5,449,345 A | 9/1995 | Taylor et al. |
| 5,267,940 A | 12/1993 | Moulder | 5,449,368 A | 9/1995 | Kuzmak |
| 5,267,942 A | 12/1993 | Saperston | 5,456,690 A | 10/1995 | Duong-Van |
| 5,269,891 A | 12/1993 | Colin et al. | 5,461,293 A | 10/1995 | Rozman et al. |
| 5,271,395 A | 12/1993 | Wahlstrand et al. | 5,461,390 A | 10/1995 | Hoshen |
| 5,274,859 A | 1/1994 | Redman et al. | 5,464,435 A | 11/1995 | Neumann |
| 5,280,789 A | 1/1994 | Potts | 5,467,627 A | 11/1995 | Smith et al. |
| 5,282,839 A | 2/1994 | Roline et al. | 5,474,226 A | 12/1995 | Joseph |
| 5,282,840 A | 2/1994 | Hudrlik | 5,479,818 A | 1/1996 | Walter et al. |
| 5,291,894 A | 3/1994 | Nagy et al. | 5,482,049 A | 1/1996 | Addiss et al. |
| 5,292,219 A | 3/1994 | Merin et al. | 5,487,760 A | 1/1996 | Villafana |
| 5,295,967 A | 3/1994 | Rondelet et al. | 5,490,514 A | 2/1996 | Rosenberg |
| 5,298,022 A | 3/1994 | Bernardi et al. | 5,493,738 A | 2/1996 | Sanderson et al. |
| 5,298,884 A | 3/1994 | Gilmore et al. | 5,494,036 A | 2/1996 | Uber, III et al. |
| 5,300,093 A | 4/1994 | Koestner | 5,494,193 A | 2/1996 | Kirschner et al. |
| 5,300,120 A | 4/1994 | Knapp et al. | 5,504,474 A | 4/1996 | Libman et al. |
| 5,304,112 A | 4/1994 | Mrklas et al. | 5,505,916 A | 4/1996 | Berry, Jr. |
| 5,305,923 A | 4/1994 | Kirschner et al. | 5,507,412 A | 4/1996 | Ebert et al. |
| 5,312,443 A | 5/1994 | Adams et al. | 5,507,737 A | 4/1996 | Palmskog et al. |
| 5,312,452 A | 5/1994 | Salo | 5,507,785 A | 4/1996 | Deno |
| 5,312,453 A | 5/1994 | Shelton et al. | 5,509,888 A | 4/1996 | Miller |
| 5,313,953 A | 5/1994 | Yomtov et al. | 5,509,891 A | 4/1996 | DeRidder |
| 5,314,451 A | 5/1994 | Mulier | 5,513,945 A | 5/1996 | Hartmann et al. |
| 5,314,457 A | 5/1994 | Jeutter et al. | 5,514,103 A | 5/1996 | Srisathapat et al. |
| 5,324,315 A | 6/1994 | Grevious | 5,518,504 A | 5/1996 | Polyak |
| 5,325,834 A | 7/1994 | Ballheimer et al. | 5,520,606 A | 5/1996 | Schoolman et al. |
| 5,326,249 A | 7/1994 | Weissfloch et al. | 5,523,740 A | 6/1996 | Burgmann et al. |
| 5,328,460 A | 7/1994 | Lord et al. | 5,534,018 A | 7/1996 | Wahlstrand et al. |
| 5,330,511 A | 7/1994 | Boute et al. | 5,535,752 A | 7/1996 | Halperin et al. |
| 5,337,750 A | 8/1994 | Wallock | 5,538,005 A | 7/1996 | Harrison et al. |
| 5,341,430 A | 8/1994 | Aulia et al. | 5,540,731 A | 7/1996 | Testerman |
| 5,342,401 A | 8/1994 | Spano et al. | 5,541,857 A | 7/1996 | Walter et al. |
| 5,342,406 A | 8/1994 | Thompson | 5,545,140 A | 8/1996 | Conero et al. |
| 5,344,388 A | 9/1994 | Maxwell et al. | 5,545,151 A | 8/1996 | O'Connor et al. |
| 5,347,476 A | 9/1994 | McBean, Sr. | 5,545,186 A | 8/1996 | Olson et al. |
| 5,348,210 A | 9/1994 | Linzell et al. | 5,545,214 A | 8/1996 | Stevens |
| 5,348,536 A | 9/1994 | Young et al. | 5,547,470 A | 8/1996 | Johnson et al. |
| 5,350,413 A | 9/1994 | Miller et al. | 5,551,427 A | 9/1996 | Altman |
| 5,352,180 A | 10/1994 | Candelon et al. | 5,551,439 A | 9/1996 | Hickey |
| 5,353,622 A | 10/1994 | Theener | 5,554,185 A | 9/1996 | Block et al. |
| 5,353,800 A | 10/1994 | Pohndorf et al. | 5,558,644 A | 9/1996 | Boyd et al. |
| 5,354,200 A | 10/1994 | Klein et al. | 5,564,434 A | 10/1996 | Halperin et al. |
| 5,354,316 A | 10/1994 | Keimel | 5,575,770 A | 11/1996 | Melsky et al. |
| 5,354,319 A | 10/1994 | Wyborny et al. | 5,584,803 A | 12/1996 | Stevens et al. |
| 5,360,407 A | 11/1994 | Leonard et al. | 5,586,629 A | 12/1996 | Shoberg et al. |
| 5,365,462 A | 11/1994 | McBean, Sr. | 5,591,171 A | 1/1997 | Brown |
| 5,365,619 A | 11/1994 | Solomon | 5,592,939 A | 1/1997 | Martinelli |
| 5,365,985 A | 11/1994 | Todd et al. | 5,593,430 A | 1/1997 | Renger |
| 5,368,040 A | 11/1994 | Carney | 5,594,665 A | 1/1997 | Walter et al. |
| 5,370,665 A | 12/1994 | Hudrlik | 5,596,986 A | 1/1997 | Goldfarb |
| 5,373,852 A | 12/1994 | Harrison et al. | 5,597,284 A | 1/1997 | Weltlich et al. |
| 5,375,073 A | 12/1994 | McBean | 5,610,083 A | 3/1997 | Chan et al. |
| 5,377,128 A | 12/1994 | McBean | 5,611,768 A | 3/1997 | Tutrone, Jr. |
| 5,378,231 A | 1/1995 | Johnson et al. | 5,612,497 A | 3/1997 | Walter et al. |
| 5,382,232 A | 1/1995 | Hague et al. | 5,615,671 A | 4/1997 | Schoonen et al. |
| 5,383,915 A | 1/1995 | Adams | 5,619,991 A | 4/1997 | Sloane |
| 5,388,578 A | 2/1995 | Yomtov et al. | 5,622,869 A | 4/1997 | Lewis et al. |
| 5,388,586 A | 2/1995 | Lee et al. | 5,625,946 A | 5/1997 | Wildeson et al. |
| 5,388,831 A | 2/1995 | Quadri et al. | 5,626,623 A | 5/1997 | Kieval et al. |

| | | | | | |
|---|---|---|---|---|---|
| 5,626,630 A | 5/1997 | Markowitz et al. | 5,957,861 A | 9/1999 | Combs et al. |
| 5,630,836 A | 5/1997 | Prem et al. | 5,967,986 A | 10/1999 | Cimochowski et al. |
| 5,634,255 A | 6/1997 | Bishop et al. | 5,970,801 A | 10/1999 | Ciobanu et al. |
| 5,637,083 A | 6/1997 | Bertrand et al. | 5,971,934 A | 10/1999 | Scherer et al. |
| 5,643,207 A | 7/1997 | Rise | 5,974,873 A | 11/1999 | Nelson et al. |
| 5,645,065 A | 7/1997 | Shapiro et al. | 5,978,985 A | 11/1999 | Thurman |
| 5,645,116 A | 7/1997 | McDonald | 5,991,664 A | 11/1999 | Seligman |
| 5,650,766 A | 7/1997 | Burgmann et al. | 5,993,395 A | 11/1999 | Shulze |
| 5,673,585 A | 10/1997 | Bishop et al. | 5,993,398 A | 11/1999 | Alperin |
| 5,676,690 A | 10/1997 | Noren et al. | 5,995,874 A | 11/1999 | Borza et al. |
| 5,681,285 A | 10/1997 | Ford et al. | 6,009,878 A | 1/2000 | Weijand et al. |
| 5,686,831 A | 11/1997 | Vandervalk et al. | 6,010,482 A | 1/2000 | Kriesel et al. |
| 5,687,734 A | 11/1997 | Dempsey et al. | 6,015,386 A | 1/2000 | Kensey et al. |
| 5,693,076 A | 12/1997 | Kaemmerer | 6,015,387 A | 1/2000 | Schwartz et al. |
| 5,702,368 A | 12/1997 | Stevens et al. | 6,019,729 A | 2/2000 | Itoigawa et al. |
| 5,702,427 A | 12/1997 | Ecker et al. | 6,024,704 A | 2/2000 | Meador et al. |
| 5,702,431 A | 12/1997 | Wang et al. | 6,030,413 A | 2/2000 | Lazarus |
| 5,704,352 A | 1/1998 | Tremblay et al. | 6,035,461 A | 3/2000 | Nguyen |
| 5,711,302 A | 1/1998 | Lampropoulos et al. | 6,053,873 A | 4/2000 | Govari et al. |
| 5,715,786 A | 2/1998 | Seiberth et al. | 6,056,723 A | 5/2000 | Donlon |
| 5,715,837 A | 2/1998 | Chen | 6,058,330 A | 5/2000 | Borza et al. |
| 5,716,342 A | 2/1998 | Dumbraveanu et al. | 6,059,757 A | 5/2000 | Macoviak et al. |
| 5,720,436 A | 2/1998 | Buschor et al. | 6,067,474 A | 5/2000 | Schulman et al. |
| 5,721,382 A | 2/1998 | Kriesel et al. | 6,067,991 A | 5/2000 | Forsell et al. |
| 5,730,101 A | 3/1998 | Aupperle et al. | 6,071,267 A | 6/2000 | Zamierowski |
| 5,732,710 A | 3/1998 | Rabinovich et al. | 6,076,016 A | 6/2000 | Feierbach |
| 5,733,313 A | 3/1998 | Barreras, Sr. et al. | 6,083,174 A | 7/2000 | Brehmeier-Flick et al. |
| 5,738,652 A | 4/1998 | Boyd et al. | 6,089,831 A | 7/2000 | Bruehmann et al. |
| 5,742,233 A | 4/1998 | Hoffman et al. | 6,090,096 A | 7/2000 | St. Goar et al. |
| 5,743,267 A | 4/1998 | Nikolic et al. | 6,102,678 A | 8/2000 | Peciat et al. |
| 5,749,369 A | 5/1998 | Rabinovich et al. | 6,102,856 A | 8/2000 | Groff et al. |
| 5,749,909 A | 5/1998 | Schroeppel et al. | 6,102,922 A | 8/2000 | Jakobsson et al. |
| 5,755,687 A | 5/1998 | Donion | 6,106,477 A | 8/2000 | Miesel et al. |
| 5,755,748 A | 5/1998 | Borza et al. | 6,106,551 A | 8/2000 | Crossett et al. |
| 5,765,568 A | 6/1998 | Sweezer, Jr. et al. | 6,110,145 A | 8/2000 | Macoviak |
| 5,769,812 A | 6/1998 | Stevens et al. | 6,113,553 A | 9/2000 | Chubbuck |
| 5,771,903 A | 6/1998 | Jakobsson | 6,131,664 A | 10/2000 | Sonnier |
| 5,782,774 A | 7/1998 | Shmulewitz | 6,135,945 A | 10/2000 | Sultan |
| 5,787,520 A | 8/1998 | Dunbar | 6,152,885 A | 11/2000 | Taepke |
| 5,791,344 A | 8/1998 | Schulman et al. | 6,158,965 A | 12/2000 | Butterfield et al. |
| 5,792,094 A | 8/1998 | Stevens et al. | 6,159,156 A | 12/2000 | Van Bockel et al. |
| 5,792,179 A | 8/1998 | Sideris | 6,162,180 A | 12/2000 | Miesel et al. |
| 5,795,325 A | 8/1998 | Valley et al. | 6,162,245 A | 12/2000 | Jayaraman et al. |
| 5,796,827 A | 8/1998 | Coppersmith et al. | 6,168,614 B1 | 1/2001 | Andersen et al. |
| 5,797,403 A | 8/1998 | DiLorenzo | 6,171,252 B1 | 1/2001 | Roberts |
| 5,800,375 A | 9/1998 | Sweezer et al. | 6,210,347 B1 | 4/2001 | Forsell |
| 5,803,917 A | 9/1998 | Butter field et al. | 6,216,028 B1 | 4/2001 | Haynor et al. |
| 5,807,265 A | 9/1998 | Itoigawa et al. | 6,234,745 B1 | 5/2001 | Pugh et al. |
| 5,807,336 A | 9/1998 | Russo et al. | 6,240,316 B1 | 5/2001 | Richmond et al. |
| 5,810,015 A | 9/1998 | Flaherty | 6,240,318 B1 | 5/2001 | Phillips |
| 5,810,757 A | 9/1998 | Sweezer, Jr. et al. | 6,245,102 B1 | 6/2001 | Jayaraman |
| 5,810,841 A | 9/1998 | McNeirney et al. | 6,248,080 B1 | 6/2001 | Miesel et al. |
| 5,814,016 A | 9/1998 | Valley et al. | 6,251,093 B1 | 6/2001 | Valley et al. |
| 5,817,093 A | 10/1998 | Williamson, IV et al. | 6,269,819 B1 | 8/2001 | Oz et al. |
| 5,833,603 A | 11/1998 | Kovacs et al. | 6,270,482 B1 * | 8/2001 | Rosoff et al. ................. 604/200 |
| 5,836,300 A | 11/1998 | Mault | 6,277,078 B1 | 8/2001 | Porat et al. |
| 5,836,886 A | 11/1998 | Itoigawa et al. | 6,285,897 B1 | 9/2001 | Kilcoyne et al. |
| 5,840,081 A | 11/1998 | Anderson et al. | 6,292,697 B1 | 9/2001 | Roberts |
| 5,849,225 A | 12/1998 | Ebina et al. | 6,305,381 B1 | 10/2001 | Weijand et al. |
| 5,855,597 A | 1/1999 | Jayaraman et al. | 6,309,350 B1 | 10/2001 | Van Tassel et al. |
| 5,855,601 A | 1/1999 | Bessler et al. | 6,315,769 B1 | 11/2001 | Peer et al. |
| 5,860,938 A | 1/1999 | LaFontaine et al. | 6,319,208 B1 | 11/2001 | Abita et al. |
| 5,861,018 A | 1/1999 | Feierbach | 6,328,699 B1 | 12/2001 | Eigler et al. |
| 5,863,366 A | 1/1999 | Snow | 6,338,735 B1 | 1/2002 | Stevens |
| 5,868,702 A | 2/1999 | Stevens et al. | 6,357,438 B1 | 3/2002 | Hansen |
| 5,873,837 A | 2/1999 | Lieber et al. | 6,360,122 B1 | 3/2002 | Fischell et al. |
| 5,875,953 A | 3/1999 | Shioya et al. | 6,360,822 B1 | 3/2002 | Robertson et al. |
| 5,879,499 A | 3/1999 | Corvi | 6,366,799 B1 | 4/2002 | Acker et al. |
| 5,881,919 A | 3/1999 | Womac et al. | 6,366,817 B1 | 4/2002 | Kung |
| 5,885,238 A | 3/1999 | Stevens et al. | 6,379,308 B1 | 4/2002 | Brockway et al. |
| 5,887,475 A | 3/1999 | Muldner | 6,379,380 B1 | 4/2002 | Satz |
| 5,899,927 A | 5/1999 | Ecker et al. | 6,398,752 B1 | 6/2002 | Sweezer, Jr. et al. |
| 5,916,179 A | 6/1999 | Sharrock | 6,409,674 B1 | 6/2002 | Brockway et al. |
| 5,916,237 A | 6/1999 | Schu | 6,416,291 B1 | 7/2002 | Butterfield et al. |
| 5,928,182 A | 7/1999 | Kraus et al. | 6,423,031 B1 | 7/2002 | Donlon |
| 5,935,078 A | 8/1999 | Feierbach | 6,430,444 B1 | 8/2002 | Borza et al. |
| 5,935,083 A | 8/1999 | Williams | 6,431,175 B1 | 8/2002 | Penner et al. |
| 5,938,669 A | 8/1999 | Klaiber et al. | 6,432,040 B1 | 8/2002 | Meah |
| 5,951,487 A | 9/1999 | Brehmeier-Flick et al. | 6,443,887 B1 | 9/2002 | Derus et al. |

| | | | | | | |
|---|---|---|---|---|---|---|
| 6,443,893 B1 | 9/2002 | Schnakenberg et al. | | 6,915,165 B2 | 7/2005 | Forsell et al. |
| 6,450,173 B1 | 9/2002 | Forsell | | 6,926,246 B2 | 8/2005 | Ginggen et al. |
| 6,450,543 B1 | 9/2002 | Fukano et al. | | 6,929,653 B2 | 8/2005 | Strecter |
| 6,450,946 B1 | 9/2002 | Forsell | | 6,932,792 B1 | 8/2005 | St. Goar et al. |
| 6,453,907 B1 | 9/2002 | Forsell et al. | | 6,951,229 B2 | 10/2005 | Garrison et al. |
| 6,454,698 B1 | 9/2002 | Forsell et al. | | 6,951,571 B1 | 10/2005 | Srivastava |
| 6,454,699 B1 | 9/2002 | Forsell | | 6,953,429 B2 | 10/2005 | Forsell et al. |
| 6,454,700 B1 | 9/2002 | Forsell | | 6,961,619 B2 | 11/2005 | Casey |
| 6,454,701 B1 | 9/2002 | Forsell | | 6,970,742 B2 | 11/2005 | Mann et al. |
| 6,460,543 B1 | 10/2002 | Forsell et al. | | 6,979,350 B2 | 12/2005 | Moll et al. |
| 6,461,292 B1 | 10/2002 | Forsell et al. | | 6,985,078 B2 | 1/2006 | Suzuki et al. |
| 6,461,293 B1 | 10/2002 | Forsell | | 6,989,027 B2 | 1/2006 | Allen et al. |
| 6,463,329 B1 | 10/2002 | Goedeke | | 7,011,095 B2 | 3/2006 | Wolf et al. |
| 6,463,935 B1 | 10/2002 | Forsell | | 7,011,624 B2 | 3/2006 | Forsell et al. |
| 6,464,628 B1 | 10/2002 | Forsell | | 7,017,583 B2 | 3/2006 | Forsell et al. |
| 6,470,212 B1 | 10/2002 | Weijand et al. | | 7,018,406 B2 | 3/2006 | Seguin et al. |
| 6,470,213 B1 | 10/2002 | Alley | | 7,021,402 B2 | 4/2006 | Beato et al. |
| 6,470,892 B1 | 10/2002 | Forsell | | 7,025,727 B2 | 4/2006 | Brockway et al. |
| 6,471,635 B1 | 10/2002 | Forsell | | 7,044,920 B2 | 5/2006 | Letort et al. |
| 6,475,136 B1 | 11/2002 | Forsell | | 7,060,080 B2 | 6/2006 | Bachmann et al. |
| 6,475,170 B1 | 11/2002 | Doron et al. | | 7,081,683 B2 | 7/2006 | Ariav et al. |
| 6,481,292 B1 | 11/2002 | Reich | | 7,109,933 B2 | 9/2006 | Ito et al. |
| 6,482,145 B1 | 11/2002 | Forsell | | 7,131,447 B2 | 11/2006 | Sterman et al. |
| 6,482,171 B1 | 11/2002 | Corvi et al. | | 7,131,945 B2 | 11/2006 | Fink et al. |
| 6,482,177 B1 | 11/2002 | Leinders et al. | | 7,134,580 B2 | 11/2006 | Garrison et al. |
| 6,486,588 B2 | 11/2002 | Doron et al. | | 7,143,462 B2 | 12/2006 | Hohlbein |
| 6,503,189 B1 | 1/2003 | Forsell et al. | | 7,144,400 B2 | 12/2006 | Byrum et al. |
| 6,503,208 B1 | 1/2003 | Skovlund et al. | | 7,147,640 B2 | 12/2006 | Huebner et al. |
| 6,504,286 B1 | 1/2003 | Porat et al. | | 7,153,262 B2 | 12/2006 | Stivoric et al. |
| 6,505,062 B1 | 1/2003 | Ritter et al. | | 7,187,978 B2 | 3/2007 | Malek et al. |
| 6,511,490 B2 | 1/2003 | Robert | | 7,225,032 B2 | 5/2007 | Schmeling et al. |
| 6,516,062 B1 | 2/2003 | Yang et al. | | 7,257,438 B2 | 8/2007 | Kinast |
| 6,516,212 B1 | 2/2003 | Bladen et al. | | 7,285,090 B2 | 10/2007 | Stivoric et al. |
| 6,531,739 B2 | 3/2003 | Cable et al. | | 2001/0011543 A1 | 8/2001 | Forsell |
| 6,533,719 B2 | 3/2003 | Kuyava et al. | | 2001/0041823 A1 | 11/2001 | Snyder et al. |
| 6,533,733 B1 | 3/2003 | Ericson et al. | | 2002/0049394 A1 | 4/2002 | Roy et al. |
| 6,542,350 B1 | 4/2003 | Rogers | | 2002/0120200 A1 | 8/2002 | Brockway et al. |
| 6,543,907 B2 | 4/2003 | Nishiyama et al. | | 2002/0138009 A1 | 9/2002 | Brockway et al. |
| 6,558,321 B1 | 5/2003 | Burd et al. | | 2002/0177782 A1 | 11/2002 | Penner |
| 6,558,994 B2 | 5/2003 | Cha et al. | | 2003/0009201 A1 | 1/2003 | Forsell |
| 6,573,563 B2 | 6/2003 | Lee et al. | | 2003/1002313 | 1/2003 | Tracey |
| 6,582,462 B1 | 6/2003 | Andersen et al. | | 2003/0030893 A1 | 2/2003 | Cornelius et al. |
| 6,587,709 B2 | 7/2003 | Solf et al. | | 2003/0032857 A1 | 2/2003 | Forsell |
| 6,589,189 B2 | 7/2003 | Meyerson et al. | | 2003/0037591 A1 | 2/2003 | Ashton et al. |
| 6,599,250 B2 | 7/2003 | Webb et al. | | 2003/0045775 A1 | 3/2003 | Forsell |
| 6,605,112 B1 | 8/2003 | Moll et al. | | 2003/0066536 A1 | 4/2003 | Forsell |
| 6,629,534 B1 | 10/2003 | St. Goar et al. | | 2003/0088148 A1 | 5/2003 | Forsell |
| 6,640,137 B2 | 10/2003 | MacDonald | | 2003/0092962 A1 | 5/2003 | Forsell |
| 6,641,610 B2 | 11/2003 | Wolf et al. | | 2003/0093117 A1 | 5/2003 | Saadat |
| 6,645,143 B2 | 11/2003 | Van Tassel et al. | | 2003/0100929 A1 | 5/2003 | Forsell |
| 6,654,629 B2 | 11/2003 | Montegrande | | 2003/0105385 A1 | 6/2003 | Forsell |
| 6,673,109 B2 | 1/2004 | Cox | | 2003/0109771 A1 | 6/2003 | Forsell |
| 6,678,561 B2 | 1/2004 | Forsell et al. | | 2003/0114729 A1 | 6/2003 | Forsell |
| 6,682,480 B1 | 1/2004 | Habib et al. | | 2003/0120150 A1 | 6/2003 | Govari |
| 6,682,503 B1 | 1/2004 | Fariss et al. | | 2003/0125605 A1 | 7/2003 | Forsell |
| 6,682,559 B2 | 1/2004 | Myers | | 2003/0125768 A1 | 7/2003 | Peter |
| 6,689,046 B2 | 2/2004 | Sayet et al. | | 2003/0135089 A1 | 7/2003 | Forsell |
| 6,690,963 B2 | 2/2004 | Ben-Haim et al. | | 2003/0135090 A1 | 7/2003 | Forsell |
| 6,695,866 B1 | 2/2004 | Kuehn et al. | | 2003/0136417 A1 | 7/2003 | Fonseca et al. |
| 6,709,385 B2 | 3/2004 | Forsell et al. | | 2003/0144648 A1 | 7/2003 | Forsell |
| 6,718,200 B2 | 4/2004 | Marmaropoulos et al. | | 2003/0163079 A1 | 8/2003 | Burnett |
| 6,719,787 B2 | 4/2004 | Cox | | 2003/0216666 A1 | 11/2003 | Ericson et al. |
| 6,719,788 B2 | 4/2004 | Cox | | 2003/0225371 A1 | 12/2003 | Hadzic et al. |
| 6,719,789 B2 | 4/2004 | Cox | | 2004/0014456 A1 | 1/2004 | Vnnen |
| 6,731,976 B2 | 5/2004 | Penn et al. | | 2004/0016874 A1 | 1/2004 | Rao et al. |
| 6,733,525 B2 | 5/2004 | Pease et al. | | 2004/0039256 A1 | 2/2004 | Kawatahara et al. |
| 6,736,846 B2 | 5/2004 | Cox | | 2004/0054351 A1 | 3/2004 | Deniega et al. |
| 6,752,813 B2 | 6/2004 | Goldfarb et al. | | 2004/0054352 A1 | 3/2004 | Adams et al. |
| 6,757,557 B1 | 6/2004 | Bladen et al. | | 2004/0055610 A1 | 3/2004 | Forsell |
| 6,779,851 B2 | 8/2004 | Bouchiere | | 2004/0064030 A1 | 4/2004 | Forsell |
| 6,796,942 B1 | 9/2004 | Kreiner et al. | | 2004/0082867 A1 | 4/2004 | Esch et al. |
| 6,822,343 B2 | 11/2004 | Estevez | | 2004/0082904 A1 | 4/2004 | Houde et al. |
| 6,851,628 B1 | 2/2005 | Garrison et al. | | 2004/0113790 A1 | 6/2004 | Hamel et al. |
| 6,855,115 B2 | 2/2005 | Fonseca et al. | | 2004/0133092 A1 | 7/2004 | Kain |
| 6,889,772 B2 | 5/2005 | Buytaeft et al. | | 2004/0143212 A1 | 7/2004 | Trombley et al. |
| 6,890,300 B2 | 5/2005 | Lloyd et al. | | 2004/0147969 A1 | 7/2004 | Mann et al. |
| 6,896,651 B2 | 5/2005 | Gross et al. | | 2004/0172087 A1 | 9/2004 | Forsell |
| 6,896,690 B1 | 5/2005 | Lambrecht et al. | | 2004/0186396 A1 | 9/2004 | Roy et al. |
| 6,913,600 B2 | 7/2005 | Valley et al. | | 2004/0193045 A1 | 9/2004 | Scarborough et al. |

| | | |
|---|---|---|
| 2004/0215159 A1 | 10/2004 | Forsell |
| 2004/0243148 A1 | 12/2004 | Wasielewski |
| 2004/0254537 A1 | 12/2004 | Conlon et al. |
| 2005/0004516 A1 | 1/2005 | Vanney |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0027998 A1 | 2/2005 | Teglia et al. |
| 2005/0038328 A1 | 2/2005 | Stoehrer et al. |
| 2005/0061079 A1 | 3/2005 | Schulman |
| 2005/0065450 A1 | 3/2005 | Stuebe et al. |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0203360 A1 | 9/2005 | Brauker et al. |
| 2005/0240144 A1 | 10/2005 | Wassermann et al. |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler, Jr. et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0089619 A1 | 4/2006 | Ginggen |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0118793 A1 | 6/2006 | Yang et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149161 A1 | 7/2006 | Wilson et al. |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Geber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |
| 2008/0172072 A1 | 7/2008 | Pool et al. |
| 2008/0250340 A1 | 10/2008 | Dlugos et al. |
| 2008/0250341 A1 | 10/2008 | Dlugos et al. |
| 2009/0005703 A1 | 1/2009 | Fasciano |

FOREIGN PATENT DOCUMENTS

| | | |
|---|---|---|
| CA | 1059035 | 7/1979 |
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1119469 | 3/1982 |
| CN | 1059035 | 2/1992 |
| CN | 1241003 | 1/2000 |
| DE | 9416395 | 12/1994 |
| DE | 10156494 | 6/2003 |
| EA | 4581 | 6/2004 |
| EP | 0417171 | 3/1991 |
| EP | 0508141 | 10/1992 |
| EP | 0568730 | 11/1993 |
| EP | 0605302 | 7/1994 |
| EP | 0 654 232 | 5/1995 |
| EP | 0660482 | 6/1995 |
| EP | 0714017 | 5/1996 |
| EP | 0769340 | 4/1997 |
| EP | 0846475 | 6/1998 |
| EP | 0848780 | 6/1998 |
| EP | 0876808 | 11/1998 |
| EP | 0888079 | 1/1999 |
| EP | 0914059 | 5/1999 |
| EP | 0981293 | 3/2000 |
| EP | 0997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |

| | | |
|---|---|---|
| EP | 1374758 | 1/2004 |
| EP | 1442715 | 8/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1600120 | 11/2005 |
| EP | 1609440 | 12/2005 |
| EP | 1649884 | 4/2006 |
| EP | 1674033 | 6/2006 |
| EP | 1 676 527 | 7/2006 |
| EP | 1704833 | 9/2006 |
| EP | 1 736 123 | 12/2006 |
| EP | 1799119 | 6/2007 |
| GB | 2355937 | 5/2001 |
| JP | 2006/175191 | 7/2006 |
| WO | WO 89/11244 | 11/1989 |
| WO | WO 89/11701 | 11/1989 |
| WO | WO 90/04368 | 5/1990 |
| WO | WO 95/11057 | 4/1995 |
| WO | WO 97/15351 | 5/1997 |
| WO | WO 97/33513 | 9/1997 |
| WO | WO 98/33554 | 8/1998 |
| WO | WO 98/35610 | 8/1998 |
| WO | WO 99/01063 | 1/1999 |
| WO | WO 99/18850 | 4/1999 |
| WO | WO 00/04945 | 2/2000 |
| WO | WO 00/33738 | 6/2000 |
| WO | WO 00/72899 | 12/2000 |
| WO | WO 01/04487 | 1/2001 |
| WO | WO 01/12075 | 2/2001 |
| WO | WO 01/12076 | 2/2001 |
| WO | WO 01/12077 | 2/2001 |
| WO | WO 01/12078 | 2/2001 |
| WO | WO 01/21066 | 3/2001 |
| WO | WO 01/36014 | 5/2001 |
| WO | WO 01/45485 | 6/2001 |
| WO | WO 01/45486 | 6/2001 |
| WO | WO 01/47431 | 7/2001 |
| WO | WO 01/47432 | 7/2001 |
| WO | WO 01/47433 | 7/2001 |
| WO | WO 01/47434 | 7/2001 |
| WO | WO 01/47435 | 7/2001 |
| WO | WO 01/47440 | 7/2001 |
| WO | WO 01/47575 | 7/2001 |
| WO | WO 01/48451 | 7/2001 |
| WO | WO 01/49245 | 7/2001 |
| WO | WO 01/50832 | 7/2001 |
| WO | WO 01/50833 | 7/2001 |
| WO | WO 01/54626 | 8/2001 |
| WO | WO 01/58388 | 8/2001 |
| WO | WO 01/58390 | 8/2001 |
| WO | WO 01/58391 | 8/2001 |
| WO | WO 01/58393 | 8/2001 |
| WO | WO 01/60453 | 8/2001 |
| WO | WO 01/81890 | 11/2001 |
| WO | WO 02/00118 | 1/2002 |
| WO | WO 02/15769 | 2/2002 |
| WO | WO 02/26161 | 4/2002 |
| WO | WO 02/053228 | 7/2002 |
| WO | WO 02/055126 | 7/2002 |
| WO | WO 02/058551 | 8/2002 |
| WO | WO 02/065894 | 8/2002 |
| WO | WO 02/076289 | 10/2002 |
| WO | WO 02/082984 | 10/2002 |
| WO | WO 02/089655 | 11/2002 |
| WO | WO 02/090894 | 11/2002 |
| WO | WO 02/100481 | 12/2002 |
| WO | WO 03/002192 | 1/2003 |
| WO | WO 03/002193 | 1/2003 |
| WO | WO 03/020182 | 3/2003 |
| WO | WO 03/043534 | 5/2003 |
| WO | WO 03/061467 | 7/2003 |
| WO | WO 03/061504 | 7/2003 |
| WO | WO 03/096889 | 11/2003 |
| WO | WO 2004/014245 | 2/2004 |
| WO | WO 2004/014456 | 2/2004 |
| WO | WO 2004/019773 | 3/2004 |
| WO | WO 2004/030541 | 4/2004 |
| WO | WO 2004/058101 | 7/2004 |
| WO | WO 2004/066879 | 8/2004 |
| WO | WO 2004/110263 | 12/2004 |
| WO | WO 2005/000206 | 1/2005 |
| WO | WO 2005/007075 | 1/2005 |
| WO | WO 2005/027998 | 3/2005 |
| WO | WO 2005/084544 | 9/2005 |
| WO | WO 2005/107583 | 11/2005 |
| WO | WO 2006/001851 | 1/2006 |
| WO | WO 2006/018927 | 2/2006 |
| WO | WO 2006/035446 | 4/2006 |
| WO | WO 2006/113187 | 10/2006 |
| WO | WO 2006/122285 | 11/2006 |
| WO | WO 2007/067206 | 6/2007 |
| WO | WO 2007/070906 | 6/2007 |
| WO | WO 2007/072452 | 6/2007 |
| WO | WO 2007/081304 | 7/2007 |
| WO | WO 2007/104356 | 9/2007 |
| WO | WO 2007/140430 | 12/2007 |
| WO | WO 2008/088949 | 7/2008 |

OTHER PUBLICATIONS

EP Search Report dated Jun. 13, 2007 for Application No. 07250931.
EP Search Report dated Jun. 18, 2007 for Application No. 07250932.
Kirchner, G., "Honeywell and Synopsys: Concept-to-Parts Solutions for Next Generation Rad-Hard ASICs," in online magazine Compiler, http://www.synopsys.com/news/pubs/compiler/artlead_redasic-apr05.html,(Apr. 2005), pp. 1-5.
Neukomm, P.A. et al., "Passive Wireless Actuator Control and Sensor Signal Transmission," Sensors and Actuators, A21-A23 (1990) pp. 258-262.
Lechner, W., "In Vivo Band Manometry: a New Access to Band Adjustment," Obesity Surgery, vol. 15 (2005) pp. 1432-1436.
"Wireless in Healthcare," The FocalPoint Group, www.thefpgroup.com (2004) pp. 1-85.
EPO Search Report dated Jul. 12, 2007, for EP Application No. 07250931.8.
EPO Search Report dated Jul. 23, 2007, for EP Application No. 07250932.6.
European Search Report dated May 2, 2008 for Application No. EP 06250968.
European Examination Report dated Dec. 9, 2008 for Application No. EP 06250968.
European Search Report dated Nov. 3, 2008 for Application No. EP 08251508.
European Examination Report dated Jul. 23, 2007 for Application No. EP 06253286.
European Search Report dated Sep. 28, 2006 for Application No. EP 06253286.
European Search Report dated Feb. 10, 2009 for Application No. EP 07250915.
Abstract for JP2006/175191.
European Search Report dated Jun. 19, 2009 for Application No. 09250581.
European Search Report dated Jul. 10, 2009 for Application No. 09250590.
European Search Report dated Jul. 10, 2009 for Application No. 09250600.
European Search Report dated Aug. 13, 2009 for Application No. 08251093.
International Search Report and Written Opinion dated Sep. 22, 2008 for Application No. PCT/US2008/053394.

* cited by examiner

APPARATUS FOR ADJUSTMENT AND SENSING OF GASTRIC BAND PRESSURE

PRIORITY

This application is a continuation-in-part of prior co-pending U.S. Non-Provisional application Ser. No. 11/369,389, filed Mar. 7, 2006, entitled "External Pressure-Based Gastric Band Adjustment System and Method," and published as U.S. Pub. No. 2006/0211912, which is a continuation-in-part of prior co-pending U.S. Non-Provisional application Ser. No. 11/065,410, filed Feb. 24, 2005, entitled "Device for Non-Invasive Measurement of Fluid Pressure in an Adjustable Restriction Device," and published as U.S. Pub. No. 2006/0189888. The disclosure of each of those applications and publications is incorporated by reference herein.

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device," which issued on May 30, 2000, and which is incorporated herein by reference. To the extent that an adjustable gastric band system is fluid based, those of ordinary skill in the art will appreciate that it may be advantageous to acquire data indicating the pressure of fluid in the band system. Similar advantages may be achieved with fluid-filled members implanted within the stomach cavity or elsewhere. Such pressure data may be obtained before, during, and/or after pressure adjustment, and may be useful for adjustment, diagnostic, monitoring, or other purposes. The foregoing examples are merely illustrative and not exhaustive. While a variety of techniques and devices have been used treat obesity, it is believed that no one prior to the inventors has previously made or used an invention as described in the appended claims.

BRIEF DESCRIPTION OF THE FIGURES

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
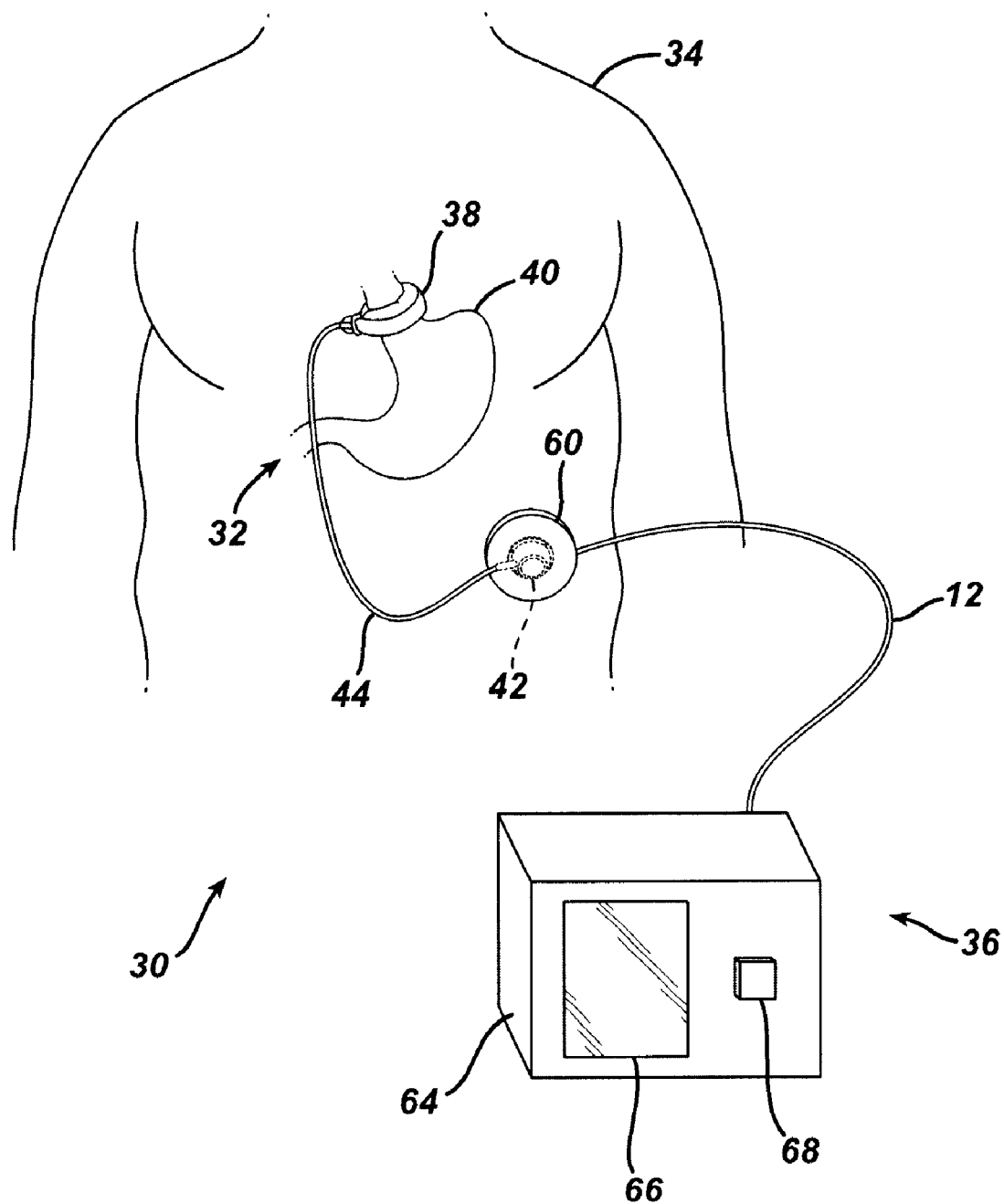
FIG. 1 is a schematic illustration of an exemplary food intake restriction system.

Referring now to the drawings in detail, wherein like numerals indicate the same elements throughout the views, FIG. 1 illustrates a food intake restriction system 30. System 30 comprises a first portion, identified generally as 32, implanted inside of a patient 34, and a second portion, identified generally as 36, located external to the patient. Implanted portion 32 comprises an adjustable gastric band 38 positioned on the upper portion of the patient's stomach 40. Adjustable band 38 may include a cavity made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. In the present example, an injection port 42, which will be described in greater detail below, is implanted in a body region accessible for needle injections and/or telemetry communication signals. In the embodiment shown, injection port 42 fluidly communicates with adjustable band 38 via a catheter 44. A surgeon may position and permanently implant injection port 42 inside the body of the patient in order to perform adjustments of the food intake restriction or stoma created by adjustable band 38. The surgeon, for example, may implant injection port 42 in the lateral, subcostal region of the patient's abdomen under the skin and layers of fatty tissue. The surgeon may also implant injection port 42 on the sternum of the patient. Of course, any other suitable implantation sites may be used.

Figure 2:
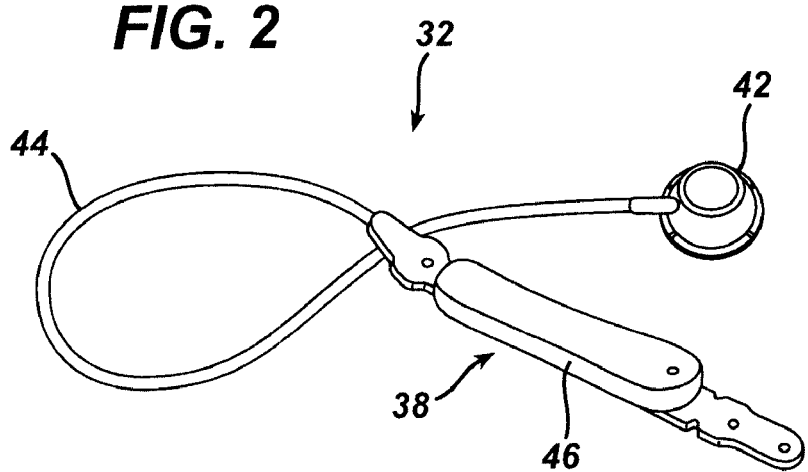
FIG. 2 is a more detailed perspective view of an exemplary implantable portion for the food intake restriction system of FIG. 1.

FIG. 2 illustrates an exemplary adjustable gastric band 38 in greater detail. In this embodiment, band 38 includes a variable volume cavity 46 that expands or contracts against the outer wall of the stomach 40 to form an adjustable stoma for controllably restricting food intake into the stomach 40. A physician may decrease the size of the stoma opening by adding fluid to variable volume cavity 46 or, alternatively, may increase the stoma size by withdrawing fluid from the cavity 46. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
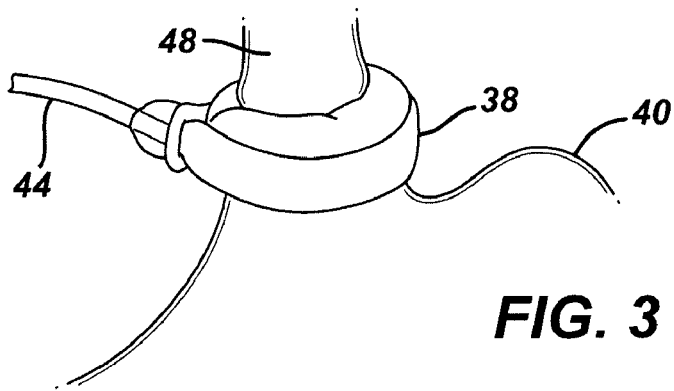
FIG. 3 is a perspective view of the adjustable gastric band of FIG. 2, showing the band positioned around the gastroesophageal junction of a patient in an exemplary use.
Figure 4:
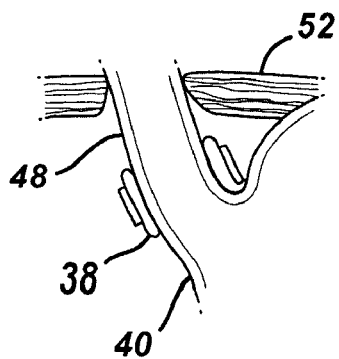
FIG. 4 is a cross-sectional view of the adjustable gastric band of FIG. 2, shown in an exemplary deflated configuration.
Figure 5:
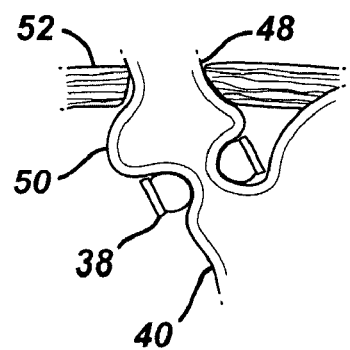
FIG. 5 is a cross-sectional view of the adjustable gastric band of FIG. 2, shown in an exemplary inflated configuration to create a food intake restriction.

FIG. 3 shows the adjustable gastric band 38 of FIG. 2 applied about the gastro-esophageal junction of a patient in an exemplary use. As shown in FIG. 3, band 38 at least substantially encloses the upper portion of stomach 40 near the junction with esophagus 48. FIG. 4 is a sectional view of band 38, showing the band 38 in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within band 38, thereby decreasing the stoma opening to create a food intake restriction. FIG. 5 also schematically illustrates the dilation of esophagus 48 above band 38 to form an upper pouch 50 beneath the diaphragm muscle 52 of the patient.

Returning now to FIG. 1, external portion 36 of food restriction system 30 comprises a pressure-reading device 60 electrically connected (in this embodiment, via an electrical cable assembly 62) to a control box 64. Control box 64 includes a display 66, one or more control switches 68, and an external control module, which will be explained in further detail below. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or pressure-reading device 60 to facilitate cleaning, maintenance, usage, and storage of external portion 36 of system 30.

Pressure-reading device 60 may non-invasively measure the pressure of the fluid within implanted portion 32 even when injection port 42 is implanted beneath thick (e.g., at least over 10 centimeters) subcutaneous fat tissue. For instance, implanted portion 32 may comprise one or more pressure sensors, and pressure-reading device 60 may be configured to obtain pressure data from implanted portion 32 via telemetry or other means. To the extent that implanted portion 32 requires power from an external source, pressure-reading device 60 or some other component, may be further configured to provide transcutaneous energy transfer (TET) to implanted portion. In the present example, a physician may hold pressure-reading device 60 against the patient's skin near the location of injection port 42 in the patient and observe the pressure reading on display 66 of control box 64. Pressure-reading device 60 may also be removably attached to the patient 34, such as during a prolonged examination, using straps, adhesives, and other well-known methods. Pressure-reading device 60 operates through conventional cloth or paper surgical drapes, and may also include a disposable cover (not shown) that may be replaced for each patient.

Figure 6:
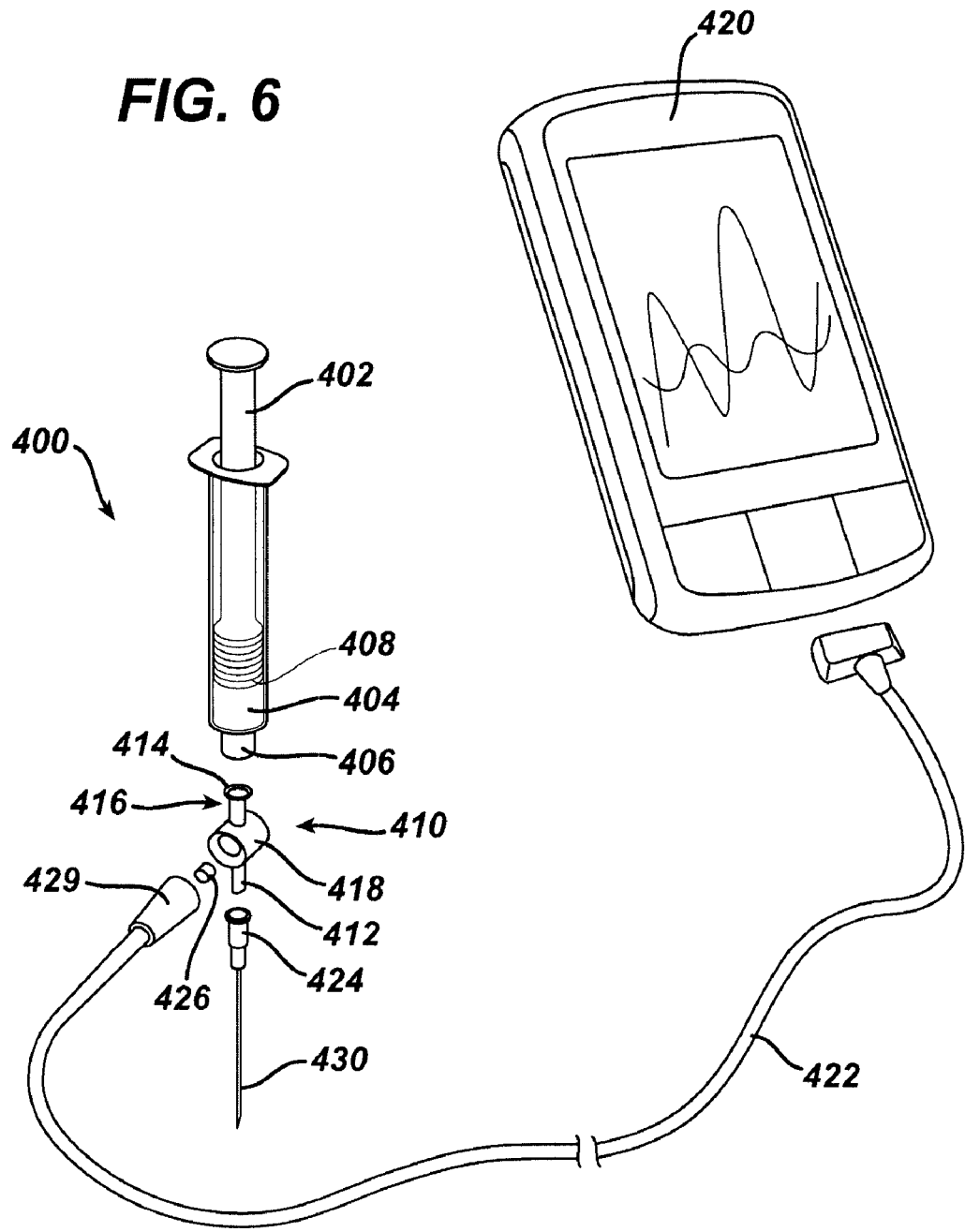
FIG. 6 is a perspective exploded view of an exemplary syringe system with pressure sensor and display device.
Figure 7:
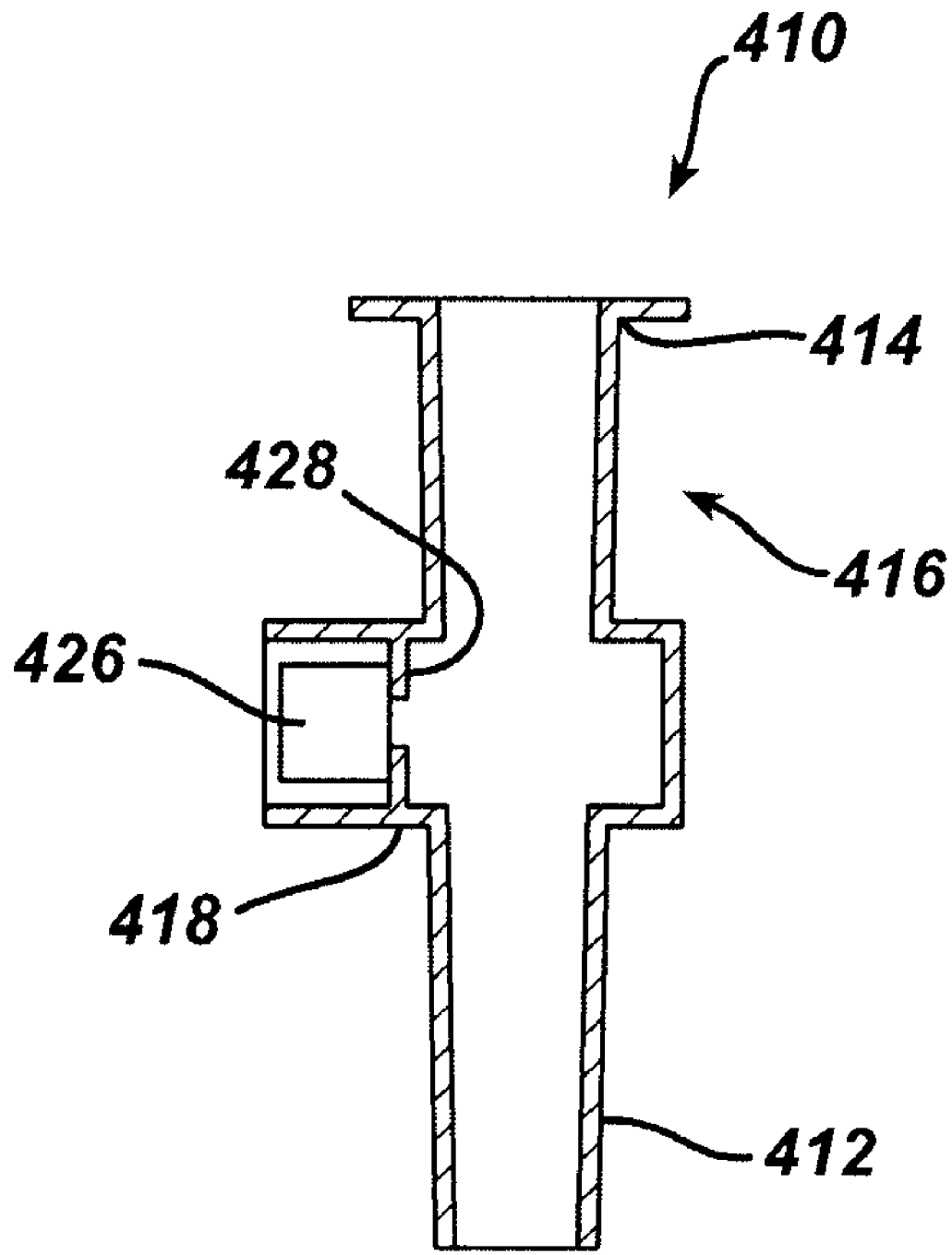
FIG. 7 is a cross-sectional view of a pressure sensing portion of the syringe system of FIG. 6.

While the above embodiments contemplate a pressure sensor being implanted within a patient 34, it will be appreciated that pressure sensors and other sensors may be provided external to a patient 34. For instance, another embodiment is shown in FIGS. 6-7, which depicts an exemplary syringe 400 and a display device 420 in communication via a cable 422. Syringe 400 comprises a plunger 402, a barrel 404, a pressure sensing component 410, and a needle 430. In the present example, plunger 402, barrel 404, and needle 430 are conventional components. Accordingly, barrel 404 has a male luer lock portion 406; and needle 430 has a female luer lock portion 424. Plunger 402 has a piston 408 configured to sealingly engage with barrel 404. In one version, needle 430 comprises a Huber needle. Of course, any of these components, among others, may be varied.

Cable 422 has a boot portion 429, which is configured to selectively attach to pressure sensing component 410. Boot portion 429 further comprises a feature (not shown) that is operable to electrically engage with pressure sensor 426, and thereby communicate pressure readings obtained by pressure sensor 426 along cable 422. Such a feature may comprise one or more terminals (not shown) or any other feature(s). In another embodiment, pressure sensing component 410 is fixedly secured to boot portion 429 and cable 422. Other suitable configurations will be apparent to those of ordinary skill in the art.

In the present example, pressure sensing component 410 comprises a male luer lock portion 412, a female luer lock portion 414, a vertical cylindraceous portion 416, a horizontal cylindraceous portion 418, and a pressure sensor 426. Male luer lock portion 412 of pressure sensing component 410 is configured to engage with female luer lock portion 424 of needle 430; while female luer lock portion 414 of pressure sensing component 410 is configured to engage with male luer lock portion 406 of barrel 404. Accordingly, it will be appreciated that pressure sensing component 410 may be retrofitted to a variety of existing syringes. Alternatively, a syringe 400 may be constructed having a pressure sensing component 410 or similar feature integrally formed within.

As shown, pressure sensor 426 is positioned within horizontal cylindraceous portion 418, adjacent to an annular flange 428. In one example, pressure sensor 426 is sealingly secured to annular flange 428. In this example, boot portion 429 comprises one or more electrodes (not shown) or similar features configured to communicate with and/or receive communications from pressure sensor 426 upon engagement of boot portion 429 with pressure sensing component 410. In another example, pressure sensor 426 is fixed within boot portion 429, and may be positioned adjacent to annular flange 428 upon engagement of boot portion 429 with pressure sensing portion 410. Alternatively, any other suitable configuration may be used.

Pressure sensor 426 may be constructed in accordance with any of the pressure sensors described above. Alternatively, pressure sensor 426 may comprise any off-the-shelf pressure sensor suitable for use, or any other type of pressure sensor. In the present example, when syringe 400 is assembled, vertical cylindraceous portion 416 provides a sealed conduit for fluid communication from barrel 404 to needle 430. Vertical cylindraceous portion 416 is further in fluid communication with horizontal cylindraceous portion 418; as is pressure sensor 426. Accordingly, it will be appreciated that pressure sensor 426 may be operable to sense pressure of fluid within syringe 400. It will also be appreciated that pressure sensed by pressure sensor 426 may be communicated to display device 420 via cable 422, and displayed thereon in any suitable format.

In one exemplary use, needle 430 is inserted into patient 34 to reach a septum of an injection port 42. Any suitable port may be used, including but not limited to a port 42 lacking a pressure sensor. Upon such insertion in the present example, needle 430 may be placed in fluid communication with implanted portion 32, such that the pressure of the fluid in implanted portion 32 and the fluid in syringe 400 may be substantially equalized. It will therefore be appreciated that pressure sensed by pressure sensor 426 may be indicative of the pressure of fluid within implanted portion 32. Such pressure information may be particularly useful during a process of adjusting pressure within implanted portion 32 via addition of fluid to implanted portion 32 with syringe 400 or via withdrawal of fluid from implanted portion 32 with syringe 400. In particular, syringe 400 may permit simultaneous adjustment and reading of fluid pressure.

For instance, a user may first insert needle 430 into patient 34 to reach the septum of an injection port 42. Upon pressure equalization, the user may then read the initial pressure via display device 420. It will be appreciated that pressure equalization may be determined by a pressure reading remaining substantially constant. The user may then add or withdraw fluid to or from implanted portion 32 using syringe 400, watching for changes in pressure indicated via display device 420. Because no valve or other mechanism is necessarily required to switch syringe 400 between a pressure sensing mode and an add/withdrawal mode, such pressure readings may be obtained as the user is adding or withdrawing fluid to or from implanted portion 32. Accordingly, pressure sensing component 410 and pressure sensor 426 may be considered substantially in-line with the other syringe 400 components. As used herein, the phrase "substantially in-line" shall be read to imply that fluid may be added or withdrawn with syringe 400 substantially contemporaneously with pressure sensing by pressure sensor 426; and that manipulation of a valve or other mechanism is not required to switch between an add/withdrawal mode of syringe 400 and a pressure sensing mode of syringe 400. However, the phrase "substantially in-line" shall not be read to require that a straight line must be able to intersect pressure sensor 426 and all other components of syringe 400.

Pressure readings may thus be obtained in approximately real-time, as the pressure is adjusted by the user with syringe 400. To the extent that there is a delay between the user's manipulation of syringe 400 and the time the pressure equalizes among syringe 400 and implanted portion 32, the user may simply wait until the pressure reading indicated by display device 420 becomes substantially constant. Other suitable uses for syringe 400 and display device 420 will be apparent to those of ordinary skill in the art.

Figure 8:
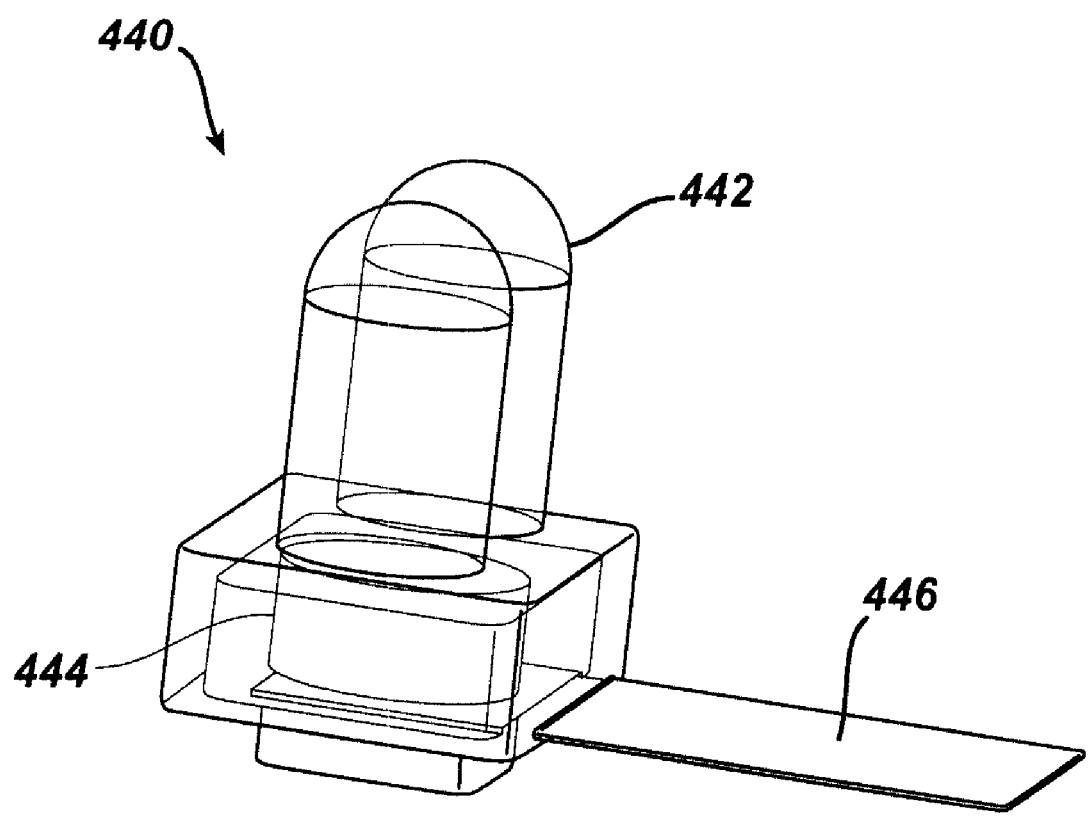
FIG. 8 is a perspective view of an exemplary infrared communicator suitable for use with the syringe system of FIG. 6.

FIG. 8 depicts an exemplary substitute for cable 422. In this variation, cable 422 of the syringe 400 version shown in FIGS. 6-7 is substituted with a wireless infrared communicator 440. Infrared communicator 440 comprises a pair of LED's 442, a battery 444, and a pull-tab 446. Infrared communicator 440 is securable to pressure sensing component 410, and is in communication with pressure sensor 426. In one embodiment, pressure sensor 426 is housed within infrared communicator 440, and is configured to be exposed to the pressure of fluid within pressure sensing component 410 when coupled with pressure sensing component 410. For instance, such pressure exposure may be provided by having pressure sensor 426 in direct contact with fluid in pressure sensing component 410. Alternatively, infrared communicator 440 and/or pressure sensing component 410 may comprise a diaphragm or other member operable to communicate pressure forces to pressure sensor 426 positioned between pressure sensor 426 and fluid in pressure sensing component 410. In yet another embodiment, pressure sensor 426 is a component of pressure sensing component 410, and infrared communicator 440 is configured to receive pressure data obtained from pressure sensor 426 when coupled with pressure sensing component 410. Still other suitable configurations will be apparent to those of ordinary skill in the art.

Infrared communicator 440 of the present example is operable to communicate pressure data obtained from pressure sensor 426 via LED's 442 in infrared light. Accordingly, it will be appreciated that display device 420 may be modified to include an infrared sensor (not shown) operable to receive such communications. Battery 444 may be used to provide power to infrared communicator 440. Pull-tab 446 may be initially positioned between battery 444 and a terminal to preserve the life of battery 444 before a first use. The user may thus remove pull-tab 446 before the first use. Alternatively, infrared communicator 440 may comprise a switch or other mechanism for selectively activating battery 444. Other variations will be apparent to those of ordinary skill in the art. In addition, it will be appreciated that the wireless nature of infrared communicator 400 or other communication devices described herein may provide a degree of patient isolation, other results, or no appreciable results. It will also be appreciated that this variation of syringe 400 may be used in a manner similar to any of the other variations of syringe 400, as described above.

Figure 9:
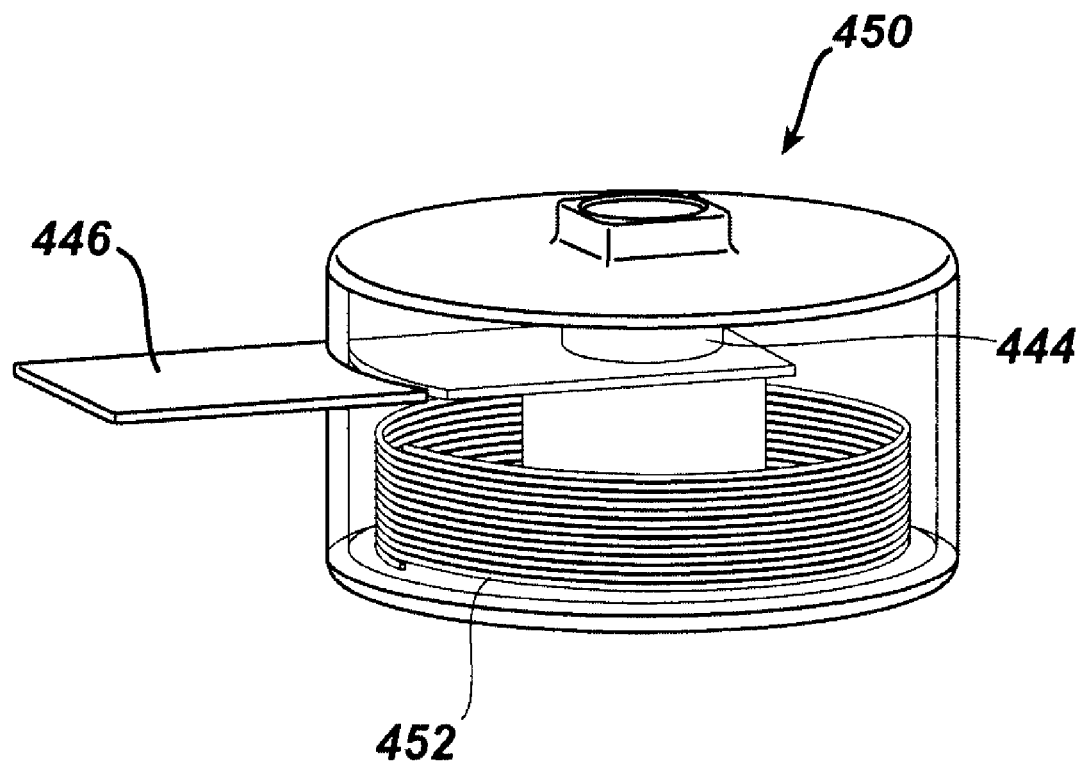
FIG. 9 is a perspective view of an exemplary RF communicator suitable for use with the syringe system of FIG. 6.

FIG. 9 shows yet another exemplary substitute for cable 422. In this variation, cable 422 of the syringe 400 version shown in FIGS. 6-7 is substituted with a wireless radio frequency (RF) communicator 450. RF communicator 450 comprises an RF coil 452, a battery 444, and a pull-tab 446. RF communicator 450 is securable to pressure sensing component 410, and is in communication with pressure sensor 426. As noted above with respect to infrared communicator 440, pressure sensor 426 may reside within RF communicator 450 or within pressure sensing component 410 other suitable configurations will be apparent to those of ordinary skill in the art.

RF communicator 450 of the present example is operable to communicate pressure data obtained from pressure sensor 426 via RF coil 452 as an RF signal. Accordingly, it will be appreciated that display device 420 may be modified to include an RF signal receiver (not shown) operable to receive such communications. Battery 444 may be used to provide power to RF communicator 450. Pull-tab 446 may be initially positioned between battery 444 and a terminal to preserve the life of battery 444 before a first use. The user may thus remove pull-tab 446 before the first use. Alternatively, RF communicator 450 may comprise a switch or other mechanism for selectively activating battery 444. Other variations will be apparent to those of ordinary skill in the art. It will also be appreciated that this variation of syringe 400 may be used in a manner similar to any of the other variations of syringe 400, as described above.

Figure 10:
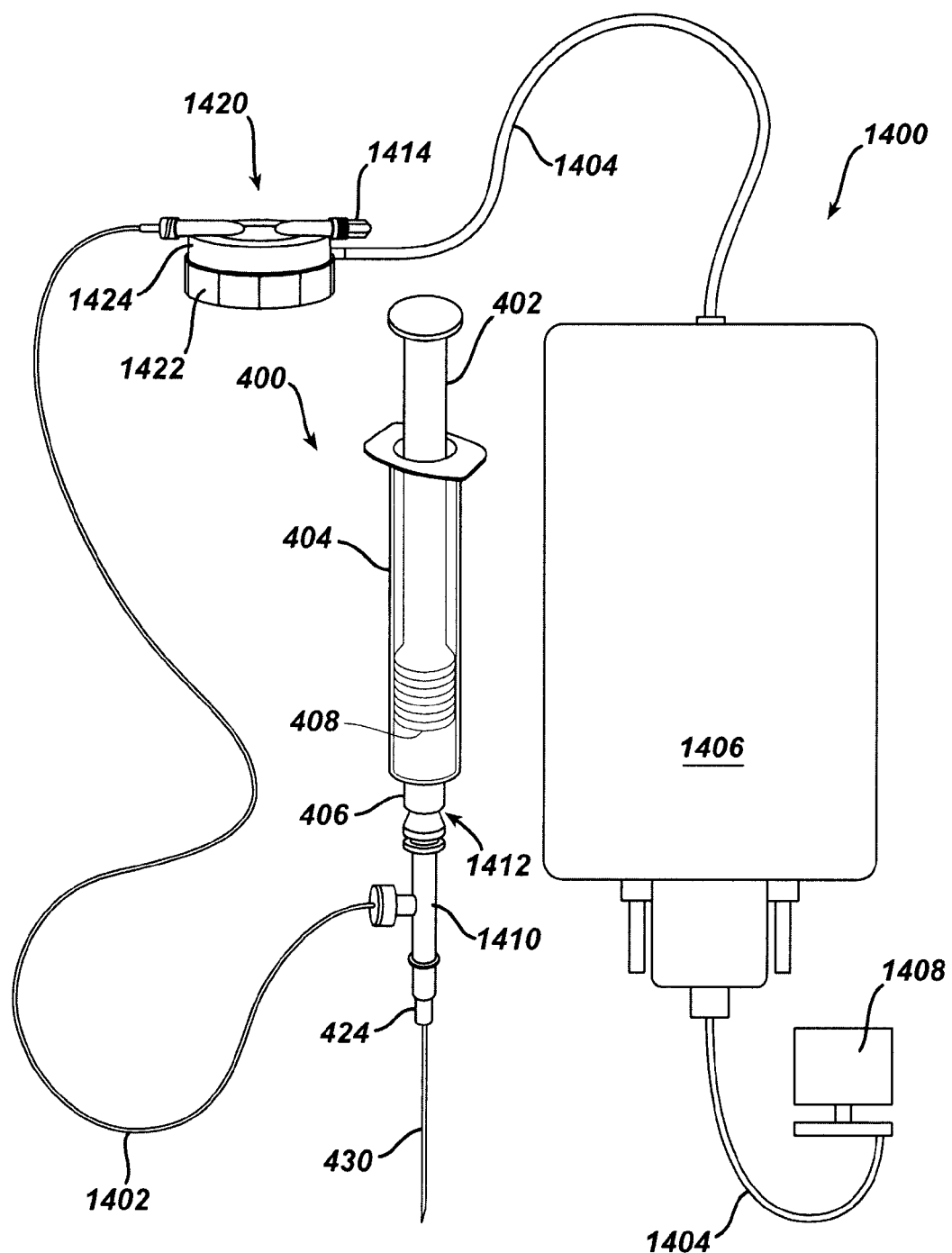
FIG. 10 is a schematic view of an alternative exemplary pressure sensing syringe system.

FIG. 10 shows another exemplary pressure sensing syringe system 1400. In this example, syringe system 1400 comprises a syringe 400, tubing 1402, a pressure sensing portion 1420, cables 1404, an interface component 1406, and a display device 1408. Syringe 400 comprises "T"-joint 1410 having a two-way leur activated valve 1412. Of course, the "T" shape of "T" joint 1410 is merely exemplary. Those of ordinary skill in the art will immediately recognize that any joint or fitting described herein may have any suitable alternative shape (e.g., "Y" shape). In the present example, "T"-joint 1410 is in fluid communication with needle 430 and tubing 1402. Two-way luer activated valve 1412 is configured such that it opens when "T"-joint 1410 is coupled with male luer lock portion 406 of syringe 400. Of course, a "T"-joint 1410 or other device may be provided without a two-way luer activated valve 1412. It will also be appreciated that pressure sensing component 410 described above may also have a two-way luer activated valve (e.g., at female luer lock portion 414). In the present example, when "T"-joint 1410 is coupled with syringe 400, tubing 1402 is operable to communicate the pressure of fluid within syringe 400 to pressure sensing portion 1420. It will be appreciated that "T"-joint may be secured to a variety of existing syringes 400 and needles 430. To the extent that a two-way luer activated valve 1412 or similar device is used (e.g., in "T"-joint 1410, in pressure sensing component 410, etc.), barrel 404 may be removed after pressure is adjusted without affecting fluid pressure in components "downstream" of two-way luer activated valve 1412. By way of example only, it may be desirable to adjust pressure using syringe 400, then remove barrel 404 from two-way luer activated valve 1412, then have patient 34 stand upright, then obtain subsequent pressure measurements. Removal of barrel 404 and/or other uses for two-way luer activated valve 1412 may also be desirable in a number of other situations.

Figure 11:
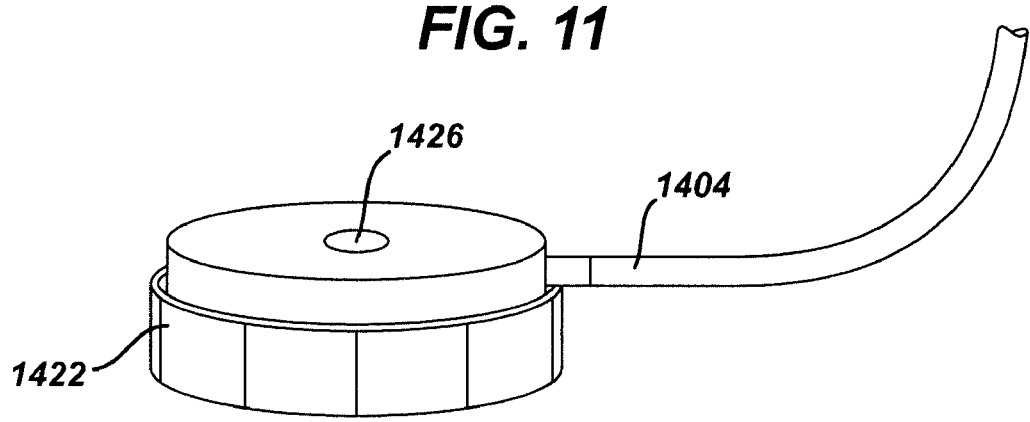
FIG. 11 is a perspective view of a reusable sensor portion of the pressure sensing syringe system of FIG. 10.
Figure 12:
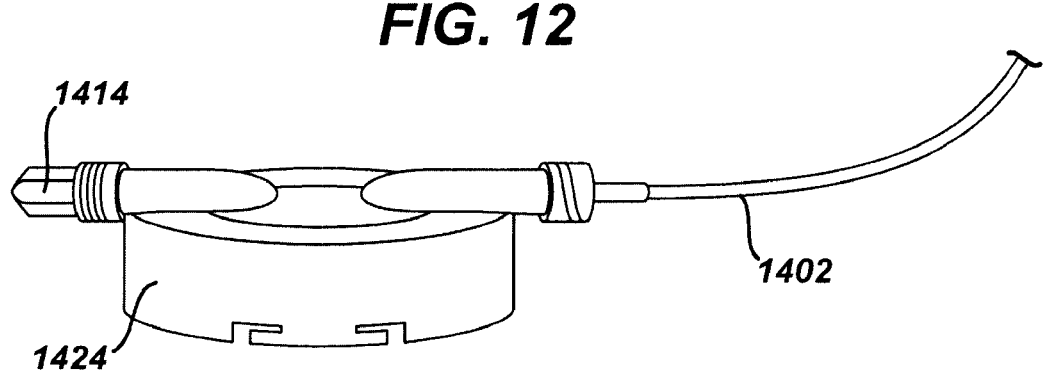
FIG. 12 is a partial perspective view of a disposable cap portion of the pressure sensing syringe system of FIG. 10.

As shown in FIGS. 10-12, pressure sensing portion 1420 comprises a reusable sensor portion 1422 and a disposable cap portion 1424. Reusable sensor portion 1422 and disposable cap portion 1424 are configured to selectively engage one another. When coupled with reusable sensor portion 1422, disposable cap portion 1424 is in fluid communication with reusable sensor portion 1422, such that pressure of fluid within tubing 1402 may be communicated to reusable sensor portion 1422 via disposable cap portion 1424. In one embodiment, disposable cap portion 1424 comprises the pressure dome described in U.S. Pat. No. 6,725,726, the disclosure of which is incorporated by reference herein. Reusable sensor portion 1422 comprises a pressure port 1426, which is configured to receive such fluid pressure communications from disposable cap portion 1424. For instance, pressure port 1426 may comprise a diaphragm or other structure suited for receiving fluid pressure communications. Reusable sensor portion 1422 further comprises a pressure sensor (not shown), such as a transducer, which is configured to provide pressure data via cable 1404 to interface component 1406. Interface component 1406 is operable to process such pressure data and communicate it to display device 1408 via cable 1404. In one embodiment, reusable sensor portion 1422 comprises a Model SP840 or SP844 sensor from MEMSCAP of Durham, N.C., though any other sensor portion 1422 component(s) may be used. Of course, interface component 1406 and display device 1408 may alternatively be integrated as a single device. Interface component 1406 and/or display device 1408 may comprise a desktop PC, a laptop computer, a personal digital assistant (PDA), a dedicated device, or any other suitable device(s).

It will be appreciated that, in order to effectively communicate the pressure of fluid in syringe 400 to reusable sensor portion 1422, it may be desirable to provide a fluid within tubing 1402. Such fluid may be provided within tubing 1402 before attempting to take pressure measurements. While the fluid within tubing 1402 may be the same type of fluid within syringe 400 (e.g. saline), any fluid may be used, including but not limited to gels, silicone fluid, saline, etc. In one embodiment, 1402 tubing is provided pre-primed, such that fluid is provided within tubing 1402 prior to use (e.g., before "T" joint 1410 is coupled with syringe 400). In another embodiment, tubing 1402 is initially empty of fluid, and the user primes tubing 1402 with fluid before using syringe 400 to add or withdraw fluid to or from injection port 42. Accordingly, a vent cap 1414 is provided in disposable cap portion 1424 to facilitate priming of tubing 1402 with fluid by facilitating the evacuation of air from tubing 1402.

As described above, a user may use syringe 400 to add fluid to or withdraw fluid from port 42 to adjust a gastric band 38. With pressure sensing syringe system 1400 assembled as shown in FIG. 10 during such use, or when any suitable variation of pressure sensing syringe system 1400 is used, it will be appreciated that fluid pressure may be sensed, and pressure measurements may be made, as gastric band 38 pressure is adjusted. In other words, pressure may be sensed and adjusted substantially simultaneously, without the need to manipulate a stopcock valve or similar device in order to switch between solely adjusting pressure or solely sensing pressure. Alternatively, such a stopcock valve or similar device may be provided.

While reusable sensor portion 1422 and disposable cap portion 1424 are shown as being separate components, it is contemplated that these components 1422, 1424 may alternatively be unitary. Still other variations will be apparent to those of ordinary skill in the art.

Figure 13:
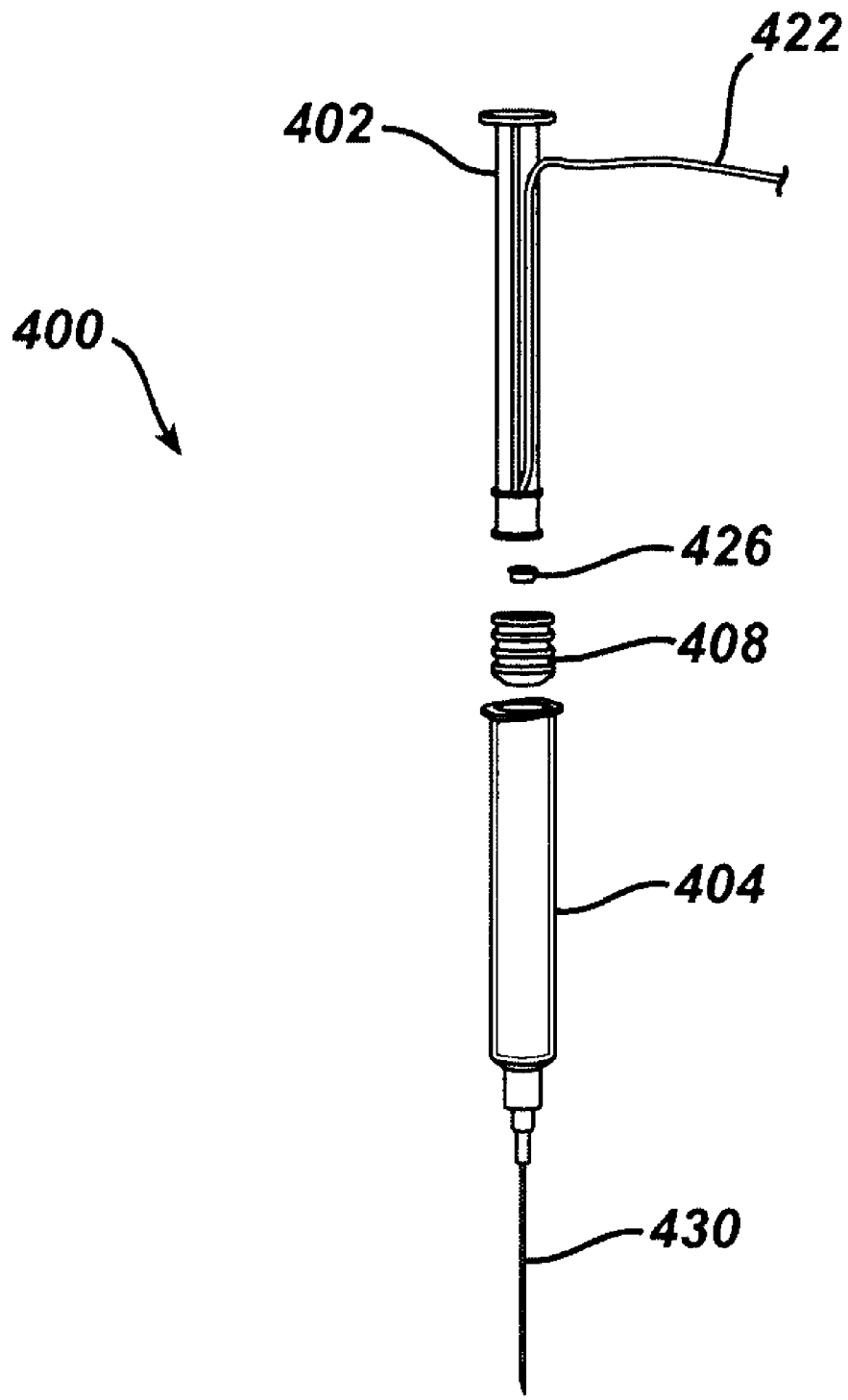
FIG. 13 is a perspective exploded view of an alternative syringe with pressure sensor.

FIG. 13 depicts a variation of syringe 400. In this variation, pressure sensor 426 is positioned between plunger 402 and piston 408, and is in communication with display device 420 via cable 422. Alternatively, pressure sensor 426 may be positioned within piston 408 or at the distal end of piston 408, such that it is in contact with fluid within barrel 404. In any of these variations, pressure sensor 426 may be configured to sense the pressure of fluid within barrel 404, and hence, the pressure of fluid within implanted portion 32 when needle 430 is placed in fluid communication with implanted portion 32. As with embodiments described above, such pressure measurements may be communicated to the user via display device 420 as the user is adding fluid to or withdrawing fluid from the implanted portion 32 via syringe 400 in approximately real-time.

The foregoing describes but a few examples of suitable locations for a pressure sensor external to a patient 34. Several other suitable locations exist, including but not limited to in barrel 404 (e.g., adjacent to male luer lock portion 406), in needle 430 (e.g., adjacent to female luer lock portion 424), or in any other suitable location. Similarly, just as syringe 400 may be varied, so may display device 420. For instance, while display device 420 of the present example is dedicated for use with pressure sensor 426, display device 420 may be any other device. By way of example only, display device 350 shown in FIG. 18 may be configured to receive communications from pressure sensor 426. Alternatively, pressure sensor 426 may be configured to communicate with a desktop PC, laptop computer, personal digital assistant (PDA), or any other device. Other variations of syringe 400 and display device 420 will be apparent to those of ordinary skill in the art, as will methods of processing pressure data. By way of example only, display device 420 or any other device may be configured to analyze pressure amplitude, the rate of change in pressure, and/or other factors to determine whether a user is using a syringe 400 that is too large, too small, or is using the syringe 400 improperly (e.g., injecting fluid too quickly, etc.), and may alert the user (e.g., visually and/or aurally) when such conditions are found.

In the present example, in any of the foregoing embodiments, it will be appreciated that and display 66 and/or display device 420 may be used to provide approximately real-time pressure measurements to a user before, during, and after the addition or withdrawal of fluid to or from implanted portion 32. For instance, a surgeon may adjust the saline content of implanted portion 32 while patient 34 swallows a fixed amount of water, and may monitor the pressure level in implanted portion via display 66 and/or display device 420 during such activities. It will be appreciated that an optimal pressure adjustment may be determined based on a variety of factors related to pressure data, including but not limited to any of the following: the original baseline pressure; the new baseline pressure; the maximum peristaltic pressure; the minimum peristaltic pressure; the length of a peristaltic contraction; the Fourier transform, Laplace transform, other transform, or other use of time/frequency domain information of a peristaltic contraction data spike; the total averaged pressure decay time constant during a water swallowing period; the number of peristaltic contractions to swallow a fixed amount of water; one or more forces exerted by an implanted device and/or an anatomical structure; energy of an implanted device or of fluid therein; the fill rate of fluid into an implanted device; the volume of fluid in an implanted device; the capacity of an implanted device; the flow rate of fluid into or within an implanted device; the pressure pulse rate of fluid within an implanted device; a counted number of pressure pulses of fluid within an implanted device; one or more electrical signals communicated from tissue prior to and/or in response to adjustment of an implanted device; chemical(s) output from tissue prior to and/or in response to adjustment of an implanted device; other tissue feedback responsive to adjustment of an implanted device; or any other factors.

In one embodiment, control box 64 or display device 420 is operable to receive data indicative of the above-noted factors in any suitable fashion (e.g., from sensors, etc.), and is further operable to automatically process such factors and present the result of such processing to the user via display 66 or display device 420. For instance, control box 64 or display device 420 may be configured to determine an ideal amount of fluid to be added or withdrawn based on such processing of factors, and may simply display a message to the user such as "Add 4 cc's of fluid," "Withdraw 0.5 cc's of fluid," or the like. Display 66 or display device 420 may also provide an indication of when the proper fluid adjustment has been completed. Such messages may be displayed in addition to or in lieu of displaying pressure measurements, changes in pressure, or other data. Other suitable processes of any of the above-noted factors or other factors, as well as ways in which results of such processes may be presented to the user, will be apparent to those of ordinary skill in the art.

As discussed above, it may be desirable to account for temperature, atmospheric pressure, and other factors when considering measurements of pressure within implanted portion 32. Accordingly, pressure-reading device 60 or any other component may receive additional data such as temperature measurements taken within implanted portion 32, and control box 64 or display device 420 may comprise logic configured to adjust pressure readings in accordance with a variety of such factors.

Figure 14:
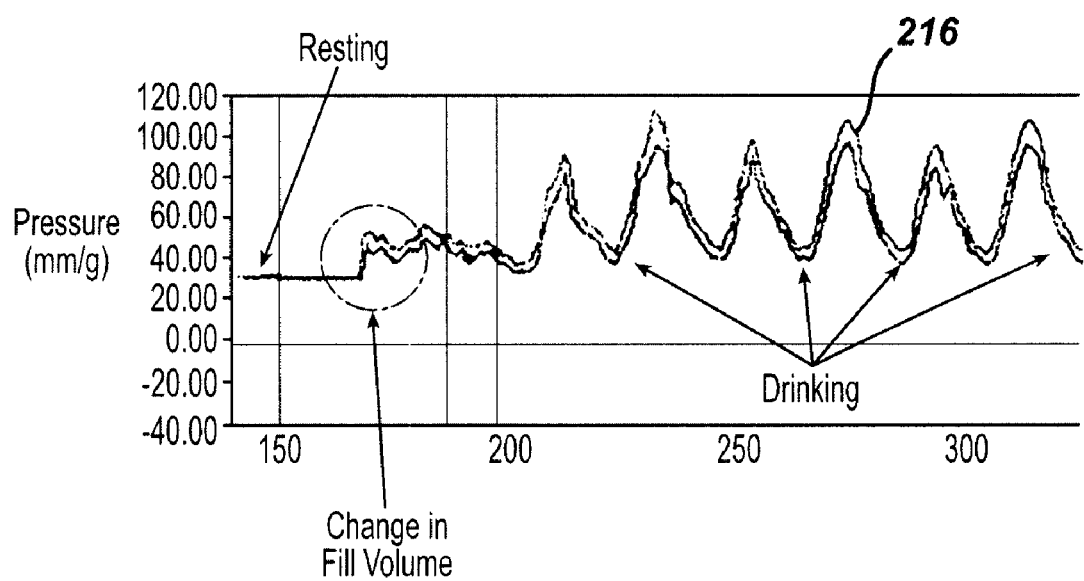
FIG. 14 is a graph indicating a pressure signal from a pressure sensing system, such as may appear on an external monitor display during interrogation by a user.

FIG. 14 is an exemplary graphical representation of a pressure signal 216 from any of the foregoing pressure sensing systems, such as may appear on display 66 or display device 420 during interrogation by a user. In one embodiment, the fluid pressure is initially measured by pressure reading device 60 or sensor 426 while the patient is stable, resulting in a steady pressure reading as shown. Next, an adjustment is applied to band 38 to decrease the stoma size. During the band adjustment, the pressure sensing system continues to measure the fluid pressure and transmit the pressure readings to control box 64 or display device 420. As seen in the graph of FIG. 14, the pressure reading rises slightly following the band adjustment. In the example shown, the patient is then asked to drink a liquid to check the accuracy of the adjustment. As the patient drinks, the pressure sensing system continues to measure the pressure spikes due to the peristaltic pressure of swallowing the liquid, and transmit the pressure readings to external module 36 for display. By measuring and visually depicting the loading of the restriction device against the peristaltic motion of the stomach both during and after an adjustment, the system of the present example provides the physician with an accurate, real-time visualization of the patient's response to the adjustment. This instantaneous, active display of recorded pressure data enables the physician to perform more accurate band adjustments. The data may be displayed over time to provide a pressure verses time history. Of course, any alternatives to a graph may be used to display pressure data, including but not limited to numbers, a moving bar, a moving needle, or any other rendering.

While the above disclosure of several embodiments explicitly describes a first instrument (e.g., syringe 400) for adjusting pressure in a gastric band 38 and a second instrument (e.g., control box 64 or display device 420), physically separate from the first instrument, for displaying sensed fluid pressure data, it will be appreciated that a pressure adjustment and sensing system may also comprise device that effects pressure adjustment and display of pressure data with a single integrated instrument. For instance, several merely exemplary integrated pressure adjustment and display systems are depicted in FIGS. 15-18, and will be described in greater detail below.

Figure 15:
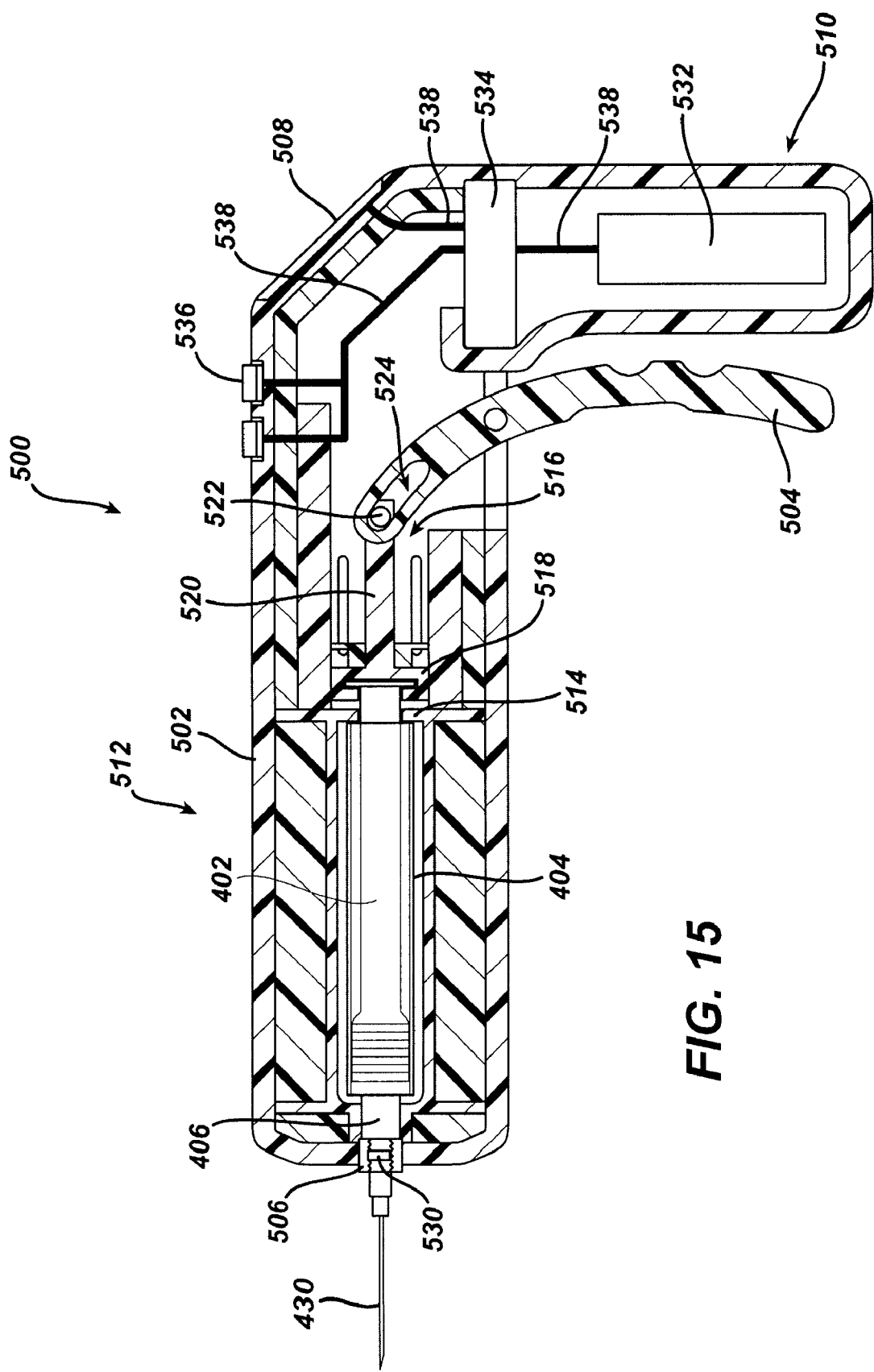
FIG. 15 is a cross-sectional side view of an alternative exemplary pressure adjustment and sensing device.

FIG. 15 shows an integrated instrument 500 comprising a housing 502, an actuator 504, a luer connector 506, and a display 508. Actuator 504 is pivotally engaged with housing 502. Housing 502 defines a handle 510 and a barrel 512. As will be described in greater detail below, handle 510 and actuator 504 are configured to permit a pistol grip type of acutation of actuator 504. As will also be described in greater detail below, barrel 512 is configured to receive components of a syringe 400. In particular, barrel 512 is configured to receive a syringe barrel 404 and plunger 402, while luer connector 506 is configured to engage with a needle 430. Instrument 500 is configured such that actuation of actuator 504 will effect actuation of syringe 400.

Within barrel 512 of instrument 500, syringe retention flange 514 extends inward to prevent proximal movement of syringe barrel 404. Luer connector 506, which is fixedly secured in the distal end of barrel 512, is configured to engage with luer lock portion 406 of syringe 400; and such engagement will prevent distal movement of syringe barrel 404. Syringe barrel 404 may therefore be fixedly secured within barrel 512 of instrument 500 in the longitudinal direction.

Luer connector 506 of the present example comprises a luer activated valve (not shown), such that fluid cannot be communicated through luer connector 506 unless luer connector 506 is connected with needle 430 or with some other component having a luer compatible fitting. Alternatively, luer activated valve may be omitted, and components described herein may fit together using any suitable non-luer interface. Furthermore, a luer activated valve may be provided elsewhere within instrument 500. In addition, any other type of valve (e.g., on/off valve, etc.) may be used to prevent fluid flow during installation of syringe barrel 404 or while inserting needle 430 into a target.

A plunger driver 516 is also provided within barrel 512 of instrument 500, and is engaged with actuator 504. Plunger driver 516 comprises a plunger engagement member 518, a stem 520, and a pin 522 that is transverse to the stem 520. Pin 522 is disposed in slot 524 of actuator 504. In this example, squeezing of actuator 504 will force plunger driver 516 distally, which will cause discharge of fluid from barrel 404 out through needle 430. In addition, if actuator 504 is forced away from handle 510, actuator 504 will pull plunger driver 516 proximally, which may effect withdrawal of fluid through needle 430 into barrel 404. Of course, as with any other components described herein, plunger driver 516 and actuator 504 may be modified, substituted, or supplemented in any suitable way.

Instrument 500 of the present example further comprises a pressure sensor 530, a power source 532, a processor 534, and buttons 536. Each of these components, as well as display 508, are in communication via electrical wires 538, though any suitable alternative for wires 538 may be used. As shown, pressure sensor 530 is provided within luer connector 506. Of course, pressure sensor 530 may be located elsewhere. In the present example, the configuration of pressure sensor 530 and luer connector 506 is such that fluid may be communicated through luer connector 506 (e.g., from barrel 404 of syringe 400 to needle 430); and pressure sensor 530 may sense pressure of fluid within luer connector 506 before, during, and/or after fluid is communicated through luer connector 506. For instance, as with any other pressure sensor described herein, pressure sensor 530 of this embodiment may be configured to sense static pressure and/or dynamic changes in pressure. Pressure sensor 530 and luer connector 506 are therefore similar to pressure sensor 426 and pressure sensing component 410, respectively, described above with respect to the embodiment illustrated in FIGS. 6-7. Signals generated by pressure sensor 530 may be communicated to processor 534 via wire 538 or otherwise.

Power source 532 may comprise any suitable type of battery or cell. By way of example only, power source 532 may comprise a rechargeable lithium ion, nickel cadmium, alkaline cell, or capacitor. Other suitable power storage technologies may also be used. Alternatively, power source 532 may be located external to instrument 500, such as a wall outlet or power generator. In another embodiment, power source 532 comprises a user's hand. Instrument 500 of the present example is configured such that power may be communicated from power source 532 to processor 534, display 508, and sensor 530 via wires 538. Processor 534 of this example is operable to process signals from sensor 530, and cause the rendering of pressure data on display 508. For instance, display 508 may render data in a manner similar to display 66 or display device 420 as described above, or in any other suitable manner. Display 508 may comprise any suitable type of display, including but not limited to LED, LCD, a graphic display, a numeric display, etc. Processor 534 is also operable to process signals from buttons 536, as will be described in greater detail below.

In the present example, instrument 500 comprises buttons 536 that are configured to be actuated by a user. For instance, buttons 536 may comprise a "+" button 536 and a "−" button 536, and may be operable to set a desired pressure level. By actuating buttons 536, a user may increase or decrease a default pressure value until the desired pressure value is displayed on display 508. Then, as the user manipulates actuator 504 to change fluid pressure within a gastric band 38 via needle 430 inserted in injection port 42, processor 534 may compare pressure data obtained using pressure sensor 530 to the preset desired pressure value that has been input via buttons 536. Display 508 may provide a visual indication when the preset desired pressure value has been reached. In addition or in the alternative, instrument 500 may provide an audio indication when the preset desired pressure value has been reached. Any suitable alternative to buttons 536 may be used to indicate a desired pressure level, including but not limited to a knob, a dial, a slider, etc. In another embodiment, processor 534 is preconfigured (e.g., "hardwired") with a desired pressure value, such that buttons 536 are omitted. It will be appreciated that display 508 may be replaced with an LED or other indicator to indicate when the preset or preconfigured pressure value is reached. In another embodiment, pressure ranges may be input via buttons 536 or otherwise, or such ranges may be preconfigured within processor 534 or a storage device. In yet another embodiment, no desired pressure value or range is input via buttons 536 or otherwise, and processor 534 is not preconfigured with any particular pressure value or range.

While not shown in the drawings, it will be appreciated that instrument 500 may also have a storage device configured to store pressure data or other data. Instrument 500 may also be configured to communicate data or commands to a remote device, or receive data or commands from a remote device, via wire or wirelessly. It will also be appreciated that various other components may be added to instrument 500, and that various components described herein may be omitted, modified, substituted, or supplemented.

Housing 502 of instrument 500 may be at least partially openable by a user, such as to insert syringe 400 components. For instance, barrel 512 may comprise a selectively removable portion of housing 502. With such a portion removed, a user may insert a conventional syringe barrel 404, with a conventional plunger 402, to fit within barrel 512 as shown in FIG. 15. Instrument 500 may thus be configured such that syringe barrel 404 and plunger 402 may "snap" into place, and such that syringe barrel 404 and plunger 402 may be replaced by a user. Alternatively, instrument 500 may be constructed such that syringe barrel 404 and plunger 402 cannot be easily accessed without destroying at least a portion of instrument 500. In another embodiment, a door (not shown) is engaged or engageable with housing 502. For instance, a door may snap onto or off of housing 502 to selectively cover or uncover syringe barrel 404 and plunger 402. Alternatively, a door may be pivotally connected to housing 502, such that it may be swung open or closed to selectively cover or uncover syringe barrel 404 and plunger 402. A door may alternatively slide relative to housing 502 or have any other type of relationship with housing 502. Furthermore, a door may be at least partially transparent to provide a window for viewing at least a portion of syringe barrel 404 and/or plunger 402. For instance, a window may be provided to permit viewing of the amount of fluid within syringe barrel 404. A window may also be provided as an opening formed through a door. Still other ways in which at least a portion of syringe barrel 404 and/or plunger 402 may be covered or uncovered within housing 502 will be apparent to those of ordinary skill in the art.

Alternatively, housing 502 may provide an open recess configured to receive syringe barrel 404 and plunger 402. For instance, housing 502 may be configured such that a syringe barrel 404 and plunger 402 may be selectively engaged and disengaged with housing 502 without requiring movement of a door or other member. In such an embodiment, structures such as inward protuberances may be used to secure syringe barrel 404 and/or plunger 402 within housing 502 upon engagement of syringe barrel 404 and/or plunger 402 with such protuberances. In other words, housing 502 may be configured such that syringe barrel 404 and/or plunger 402 can be "snapped in" or "snapped out" without requiring movement of a door or other member. Alternatively, any other suitable structures, features, or relationships between syringe barrel 404, plunger 402, and housing 502 may be employed.

Similarly, housing 502 may be constructed such that power source 532 may be easily accessed, such as for replacement or maintenance. This may include a door, protuberances, or any other structures or features described above with respect to the engagement relationship between syringe barrel 404, plunger 402, and housing 502.

In yet another variation, syringe barrel 404 and plunger 402 are substituted with a bellows reservoir (not shown). Such a bellows reservoir may be compressed or decompressed using actuator 504 to expel fluid from or withdraw fluid through needle 430. In addition, instrument 500 may be configured such that pre-filled bellows reservoirs may be inserted in barrel 512 to replace a spent bellows reservoir. Of course, any structures or devices other than syringe 400 components and bellows reservoirs may be used to store and communicate fluid via instrument 500. Still other suitable variations of instrument 500 and its components will be apparent to those of ordinary skill in the art.

Figure 16:
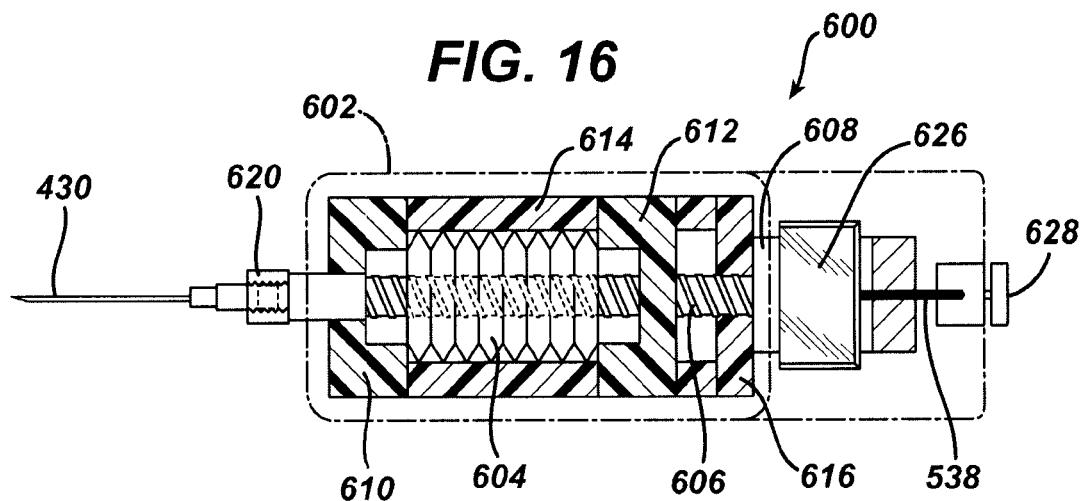
FIG. 16 is a cross-sectional plan view of another alternative exemplary pressure adjustment and sensing device.
Figure 17:
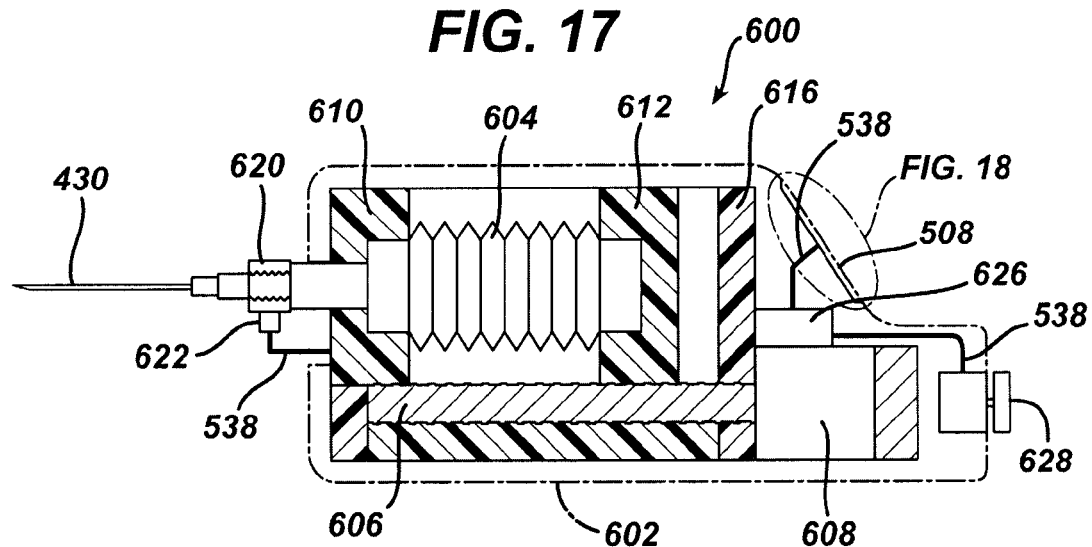
FIG. 17 is a cross-sectional side view of the device of FIG. 16.
Figure 18:
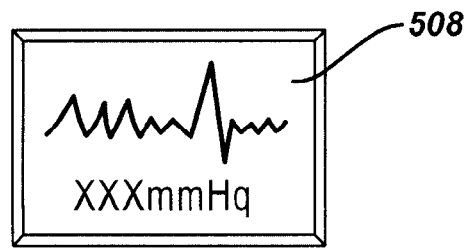
FIG. 18 is a plan view of an exemplary pressure data display.

It will also be appreciated that, while the above disclosure of several embodiments explicitly describes manually operable syringes 400 and a manually operable instrument 500 for adjusting pressure within a gastric band 38 via an injection port 42, an alternative may be to use a device that is external to a patient 34 and that is operable to adjust pressure within a gastric band 38 in an automated, semi-automated, or motorized fashion. An example of such a device is depicted in FIGS. 16-18, which shows an exemplary fluid injection instrument 600. As will be described in greater detail below, fluid injection instrument 600 comprises a housing 602, a bellows reservoir 604, a screw gear 606 operable to compress the bellows reservoir 604, and a motor 608 operable to drive the screw gear 606. Motor 608 is therefore operable to force fluid out of bellows reservoir 604 and through needle 430, which is in fluid communication with bellows reservoir 604.

Bellows reservoir 604 is secured to and positioned between a first upright member 610 and a second upright member 612. First upright member 610 is fixedly secured relative to housing 602. Second upright member 612 is slidably engaged with a pair of longitudinal rails 614, and is operable to slide distally and proximally along rails 614 within housing 602. A stop member 616 is positioned proximal to second upright member 612, and is configured to restrict proximal movement of second upright member 612. Second upright member 612 is engaged with screw gear 606 such that rotation of screw gear 606 will cause distal or proximal movement of second upright member 612, depending on the direction that screw gear 606 is rotated. However, in this example, rotation of screw gear 606 will not have any effect on first upright member 610. As noted above, rotation of screw gear 606 is effected by motor 608, with which screw gear 606 is operationally engaged. Accordingly, motor 608 may be used to effect distal and proximal movement of second upright member 612 via screw gear 606, which will in turn cause compression or expansion of bellows reservoir 612, respectively.

While bellows reservoir 604 of the present example is driven by screw gear 606, it will be appreciated that bellows reservoir 604 may be driven by a variety of alternative structures and devices. By way of example only, suitable alternatives or supplements to screw gear 606 may include, but are not limited to, slides, cams, ratchets, platenary gearing, cables, a linkage, chains, belts, rack and pinion, etc. Furthermore, bellows reservoir 604 may be substituted or supplemented by any suitable type of pump. By way of example only, suitable types of pumps may include, but are not limited to, piezo ceramic, diaphragm, peristaltic, solenoid, magnetic driven, piston, electro-kinetic, rotary vane, hand, or pneumatic, among others. To the extent that any pump is used, it may be provided as reusable, disposable, or a combination thereof, and may be in communication with a fluid reservoir via any suitable means such as a tube. Alternatively, a reservoir could be provided within a pump. Other suitable alternative mechanisms, devices, or features for expelling fluid from and/or withdrawing fluid into instrument 600 will be apparent to those of ordinary skill in the art. It will also be appreciated that any of the variations described herein relative to instrument 600 may also be incorporated into instrument 500 or into any other embodiment described herein.

Motor 608 may comprise any suitable type of motor, including but not limited to an electric motor (e.g., a stepper motor), a pneumatic motor, or any other type. Alternatively, screw gear 606 may be driven manually or by any other means. For instance, in another embodiment, motor 608 is substituted by a push/pull handle or knob, thumbwheel, rotatable dial or knob, or crank. Of course, any other suitable mechanism or device may be used as an alternative to motor 608 and/or screw gear 614. Additional components may supplement motor 608 (or a substitute for motor 608), including but not limited to an output sensitivity adjustment feature and/or an output limit adjustment feature.

It will be appreciated that bellows reservoir 612 (or any substitute for bellows reservoir 612) may be provided as a replacable component of instrument 600. For instance, bellows reservoirs 612 may be made available, pre-filled with fluid, such that a bellows reservoir 612 may be disposed of and replaced after sufficient use. Similarly, a variety of bellows reservoirs 612 may be provided having various sizes, fluid capacities, fluids types, or other properties; and a bellows reservoir 612 that is particularly appropriate for a given situation may be selected from such a group and used with instrument 600. In an alternate embodiment, where instrument 600 is used to inject medication into an implanted infuser, bellows reservoir 612 contains a medication. In any case, a bellows reservoir 612 may be provided as disposable or reusable. Of course, any suitable substitute may be made for bellows reservoir 612. For instance, bellows reservoir 612 may be substituted with one or more syringe 400 components, a saline bottle, medicinal bottle, bulb reservoir, or any other suitable device or structure. To the extent that other components of instrument 600 may need to be modified to accommodate a substitute or supplement for bellows reservoir 612, such modifications to instrument 600 components will be apparent to those of ordinary skill in the art. A bellows reservoir 612 (or a substitute thereof) may further comprise volume indication marks or other markings thereon or nearby.

Bellows reservoir 612 of the present example is in fluid communication with an outlet connector 620. Outlet connector 620 comprises a luer activated valve (not shown) and a pressure sensor 622. Outlet connector 620 is engagable with a conventional needle 430, such as a Huber needle. Outlet connector 620 and pressure sensor 622 are configured such that fluid may be communicated through outlet connector 620 (e.g., from bellows reservoir 604 to needle 430), and pressure sensor 622 may sense pressure of fluid within outlet connector 620 before, during, and/or after fluid is communicated through outlet connector 620. Pressure sensor 622 and outlet connector 620 are therefore similar to pressure sensor 530 and luer connector 506, respectively, described above with respect to the embodiment illustrated in FIG. 15.

As with any pressure sensor described herein, pressure sensor 622 may comprise any suitable type of sensor with any suitable features or components. By way of example only, suitable sensor types may include, but are not limited to, pressure, force, flow, volume, and strain, among others. Similarly, a number of sensors, including different types of sensors, may be incorporated into a single instrument 600. As shown, pressure sensor 622 is provided in outlet connector 620. To the extent that a control valve (described further below) is used, pressure sensor 622 may be integrated directly into the control valve. In another embodiment (not shown), a sensor is provided at each end of bellows reservoir 604 to measure force exerted on bellows reservoir 604 in either direction. Of course, any other types of sensors, any number of sensors, and any other suitable locations for sensors may be used.

Instrument 600 of the present example further comprises a power source 624, a processing and control circuit 626, a control knob 628, and a display 508. Power source 624 may comprise any suitable type of battery or cell. By way of example only, power source 624 may comprise a rechargeable lithium ion, nickel cadmium, or alkaline cell. Alternatively, power source 624 may be regenerative, or may comprise a solar cell. As yet another alternative, power source 624 may be located external to instrument 600, such as a wall outlet or power generator. Other suitable variations of power source 624 will be apparent to those of ordinary skill in the art.

Processing and control circuit 626 of this example is in communication with pressure sensor 622, motor 608, power source 624, and display 508 via wires 538. Any alternative 538 to wires or any alternative connection scheme may be used. Processing and control circuit 626 of this example is operable to process signals from pressure sensor 622, and to cause display 508 to render pressure data. For instance, display 508 may render data in a manner similar to display 66 or display device 420 as described above, or in any other suitable manner. Display 508 of instrument 600 may therefore be the same as display 508 of instrument 500, or either may incorporate a different display.

Processing and control circuit 626 of instrument 600 is also operable to process signals from control knob 628, as will be described in greater detail below. Processing and control circuit 626 may also provide feedback control to motor 608 for motion control algorithmic adjustments. Furthermore, a control valve (not shown) may be provided at any suitable location on or in instrument 600 (e.g., within outlet connector 620), and processing and control circuit 626 may provide control signals to control the output and/or input flow of fluid through such a control valve. Still other optional functions and communications of processing and control circuit 626 will be apparent to those of ordinary skill in the art.

As noted above, a control valve (not shown), if incorporated into an embodiment, may be provided at any suitable location on or in instrument 600. For instance, an output control valve may be provided somewhere between bellows reservoir 604 and needle 430. Such a control valve may be used to prevent the flow of fluid before use of instrument. To the extent that the control valve is a luer activated valve, connection of needle 430 to outlet connector 620 may open up the luer activated valve, allowing bidirectional or unidirectional fluid flow. It will also be appreciated that a control valve may be electrically and/or mechanically controlled for selective regulation of fluid flow. By way of example only, suitable types of control valves may include, but are not limited to, any of the following: luer activated valve, solenoid valve, needle valve, ball valve, pinch valve, stopcock, etc. Of course, a control valve may be omitted altogether.

While not shown in the drawings, it will be appreciated that instrument 600 may also have a storage device configured to store pressure data or other data. Instrument 600 may also be configured to communicate data or commands to a remote device, or receive data or commands from a remote device, via wire or wirelessly. It will also be appreciated that various other components may be added to instrument 600, and that various components described herein may be omitted, modified, substituted, or supplemented.

Operation of instrument 600 may be automated in a variety of ways and to a variety of degrees. For instance, control knob 628 may be configured such that it may be partially rotated clockwise and partially rotated counterclockwise. Control knob 628 may also be spring loaded or otherwise biased to a certain rotational position (e.g., a zero adjustment position). Partial clockwise rotation of control knob 628 may cause motor 608 to rotate such that bellows reservoir 604 is compressed, and fluid expelled through needle 430. Similarly, partial counterclockwise rotation of control knob 628 may cause motor 608 to rotate such that bellows reservoir 604 is expanded, and fluid withdrawn through needle 430. Control knob 628 may also be configured such that a partial rotation will cause expulsion or withdrawal of a predetermined certain amount of fluid from or into bellows reservoir 604 (e.g., 1 cc), with no further fluid communication being permitted until control knob 628 is returned to an original position then rotated again. Of course, control knob 628 or some substitute thereof may be used to effect fluid communication in any other suitable way.

In another embodiment, a desired pressure level is set (e.g., via control knob 628, via buttons, via some other user interface, via a predetermined pressure level "hardwired" into control circuit 626, etc.), and motor 608 is automatically rotated, with pressure feedback obtained using sensor 622, until the desired pressure level is obtained. Once the desired pressure level has been reached, motor 608 may automatically stop rotating to maintain the pressure level. Instrument 600 may also be configured to automatically stop rotating based on any other parameters or combination of parameters. Other ways in which fluid pressure may be varied and/or monitored using instrument 600 will be apparent to those of ordinary skill in the art.

While instrument 500 and instrument 600 are described herein in the context of a gastric band 38 system with an injection port 42, it will be appreciated that instrument 500 and instrument 600 (as well as any other device described herein) may be used in a variety of other contexts. By way of example only, instrument 500 or instrument 600 may be used with artificial sphincter systems, breast implants, penile implants, medication infuser pump systems, etc. Other suitable contexts and uses will be apparent to those of ordinary skill in the art. In addition, while instrument 500 and instrument 600 are shown as being handheld, either instrument 500 or instrument 600 may be mounted to a fixture, movable arm, or any other structure. Accordingly, while several exemplary integrated pressure adjustment and sensing systems, and components thereof, have been discussed above, it will be appreciated that the embodiments explicitly described are not intended to be exhaustive. Various components described above may be varied, substituted, supplemented, moved, interchanged, merged, combined, and/or separated. Suitable modifications will be apparent to those of ordinary skill in the art.

In addition to use during adjustments, the pressure sensing systems of the foregoing examples may also be used to measure pressure variations in implanted portion 32 at various intervals during treatment. Periodic pressure readings may enable the pressure sensing system to function as a diagnostic tool, to ensure that adjustable band 38 is operating effectively. In particular, a pressure sensing system may be utilized to detect a no pressure condition within band 38, which may indicate a fluid leakage or other condition. Alternatively, the system may be used to detect excessive pressure spikes within band 38, which may indicate a kink in catheter 44 or a blockage within the stoma or other conditions.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

The present invention has application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container the sealed container may keep the instrument sterile until it is opened in a medical facility. A device may also be sterilized using any other technique known in the art, including but not limited to beta or gamma radiation, ethylene oxide, or steam.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing the pressure sensor within the injection port. Alternatively, the sensor could be positioned within a fluid filled portion of the band in order to measure pressure changes within the band. Additionally, the pressure sensor could be associated with an elastomeric balloon implanted within the stomach cavity to measure fluid pressure within the balloon. The structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed is:

1. An apparatus for communicating fluid, the apparatus comprising:
   (a) a housing, wherein the housing defines an interior portion contained therein, wherein the interior portion is positioned entirely within the housing;
   (b) a fluid reservoir positioned within the interior portion of the housing, wherein the fluid reservoir is operable to hold a volume of fluid therein;
   (c) an actuator operationally engaged with the fluid reservoir, wherein the actuator is operable to effect communication of fluid from or into the fluid reservoir, wherein the actuator is positioned within the interior portion of the housing such that the actuator is confined within the interior portion;
   (d) a sensor in fluid communication with the fluid reservoir, wherein the sensor is operable to sense a physical parameter of fluid that is in communication with the fluid reservoir as the fluid is communicated from or into the fluid reservoir; and
   (e) an indicator in communication with the sensor, wherein the indicator is operable to display the physical parameter sensed by the sensor.

2. The apparatus of claim 1, wherein the fluid reservoir is defined by a syringe barrel.

3. The apparatus of claim 2, wherein the actuator comprises a syringe plunger.

4. The apparatus of claim 3, wherein the actuator further comprises a pivoting member operationally engaged with the syringe plunger.

5. The apparatus of claim 1, wherein the housing defines a handle portion and a barrel portion.

6. The apparatus of claim 5, wherein the fluid reservoir is located within the barrel portion of the housing.

7. The apparatus of claim 1, wherein the indicator comprises a display screen integrally engaged with the housing, wherein the display screen is integrated with a slanted portion of the housing.

8. The apparatus of claim 1, wherein the actuator comprises an electric motor.

9. The apparatus of claim 8, wherein the actuator further comprises a screw gear in communication with the electric motor.

10. The apparatus of claim 9, wherein the fluid reservoir comprises a bellows reservoir, wherein the screw gear is operable to compress or expand the bellows reservoir.

11. The apparatus of claim 1, wherein the fluid reservoir comprises a bellows reservoir.

12. The apparatus of claim 1, further comprising a luer interface feature, wherein the fluid reservoir is in fluid communication with the luer interface feature.

13. The apparatus of claim 12, further comprising a needle engaged with the luer interface feature.

14. The apparatus of claim 1, further comprising a user input feature configured to receive entry of one or more fluid parameter values, wherein the user input feature is engaged with the housing.

15. An apparatus for communicating fluid, the apparatus comprising:
(a) a housing defining a syringe receiving portion and a handle portion, wherein the syringe receiving portion is configured to receive a syringe barrel and a syringe plunger;
(b) an actuator mechanism, wherein the actuator mechanism comprises a stem feature, wherein the actuator mechanism is configured to engage with a syringe plunger received by the housing such that the stem feature is coaxially aligned with the syringe plunger, wherein the stem feature is movable from a first proximal position to a second distal position, wherein the stem feature of the actuator mechanism is operable to distally urge a syringe plunger within a syringe barrel, when the syringe barrel and syringe plunger are received by the syringe receiving portion, by moving the stem feature from the first proximal position to the second distal position, wherein the stem feature of the actuator mechanism is operable to proximally urge the syringe plunger within the syringe barrel, when the syringe barrel and syringe plunger are received by the syringe receiving portion, by moving the stem feature from the second distal position to the first proximal position;
(c) a sensor fixed relative to the housing, wherein the sensor is operable to sense a physical parameter associated with the communication of fluid from or into the syringe barrel; and
(d) a display in communication with the sensor, wherein the display is operable to display data based on the physical parameter sensed by the sensor.

16. The apparatus of claim 15, wherein the sensor comprises a pressure sensor.

17. The apparatus of claim 15, wherein the display is integrally engaged with the housing.

18. An apparatus for communicating fluid, the apparatus comprising:
(a) a housing;
(b) a first member and an opposingly facing second member, wherein the first member and the second member are contained within the housing, wherein the second member is configured to axially advance toward the first member;
(c) a fluid reservoir within the housing, wherein the fluid reservoir has a variable volume, wherein the fluid reservoir is held between a first plane and a second plane, wherein the first plane is defined by the first member and the second plane is defined by the second member, wherein the fluid reservoir is in communication with the first member, wherein the fluid reservoir is in further communication with the second member;
(d) a reservoir engagement mechanism engaged with the fluid reservoir, wherein the reservoir engagement mechanism is operable to selectively vary the volume of the fluid reservoir to expel fluid from or withdraw fluid into the fluid reservoir by compressing or expanding the fluid reservoir between the first member and the second member, respectively;
(e) a sensor operable to sense a physical parameter associated with the communication of fluid from or into the fluid reservoir; and
(f) a display in communication with the sensor, wherein the display is operable to render data associated with the physical parameter sensed by the sensor.

19. The apparatus of claim 18, wherein the reservoir engagement mechanism comprises a motor.

20. The apparatus of claim 18, further comprising a luer compatible feature in fluid communication with the fluid reservoir, wherein the sensor is engaged with the luer compatible feature.

* * * * *